US010492846B2

(12) United States Patent
Lambert et al.

(10) Patent No.: US 10,492,846 B2
(45) Date of Patent: Dec. 3, 2019

(54) PREDICTION OF ATRIAL WALL ELECTRICAL RECONNECTION BASED ON CONTACT FORCE MEASURED DURING RF ABLATION

(71) Applicant: St. Jude Medical International Holding S.à.r.l., Luxembourg (LU)

(72) Inventors: Hendrik Lambert, Geneva (CH); Stuart J. Olstad, Plymouth, MN (US); Olivier B. Fremont, Paris (FR)

(73) Assignee: St. Jude Medical International Holding S.á r.l., Luxembourg (LU)

( * ) Notice: Subject to any disclaimer, the term of this patent is extended or adjusted under 35 U.S.C. 154(b) by 0 days.

(21) Appl. No.: 15/352,359

(22) Filed: Nov. 15, 2016

(65) Prior Publication Data
US 2017/0128119 A1 May 11, 2017

Related U.S. Application Data

(60) Division of application No. 14/876,786, filed on Oct. 6, 2015, now abandoned, which is a continuation of
(Continued)

(51) Int. Cl.
*A61B 18/08* (2006.01)
*A61B 5/107* (2006.01)
(Continued)

(52) U.S. Cl.
CPC .......... *A61B 18/082* (2013.01); *A61B 5/1076* (2013.01); *A61B 18/10* (2013.01);
(Continued)

(58) Field of Classification Search
CPC ...... A61B 18/1492; A61B 2017/00243; A61B 2018/00577; A61B 2018/00642;
(Continued)

(56) References Cited

U.S. PATENT DOCUMENTS 4,940,064 A   7/1990  Desai
5,233,515 A   8/1993  Cosman
(Continued)

FOREIGN PATENT DOCUMENTS

CN   101309651   11/2008
CN   101558993   10/2009
(Continued)

OTHER PUBLICATIONS

Ikeda et al., "Presentation Abstract" 15841—Contact force-time integral predicts radiofequency lesion size and incidence of steam pop in the canine beating heart, Nov. 5, 2012, American Hearth Association.
(Continued)

*Primary Examiner* — Deborah L Malamud
(74) *Attorney, Agent, or Firm* — Dykema Gossett PLLC

(57) ABSTRACT

A method and device for determining the transmurality and/or continuity of an isolation line formed by a plurality of point contact ablations. In one embodiment, a method for determining the size of a lesion (width, depth and/or volume) is disclosed, based on contact force of the ablation head with the target tissue, and an energization parameter that quantifies the energy delivered to the target tissue during the duration time of the lesion formation. In another embodiment, the sequential nature (sequence in time and space) of the ablation line formation is tracked and quantified in a quantity herein referred to as the "jump index," and used in conjunction with the lesion size information to determine the probability of a gap later forming in the isolation line.

16 Claims, 9 Drawing Sheets

Related U.S. Application Data application No. 13/337,896, filed on Dec. 27, 2011, now Pat. No. 9,149,327.

(60) Provisional application No. 61/427,423, filed on Dec. 27, 2010, provisional application No. 61/427,425, filed on Dec. 27, 2010.

(51) Int. Cl.
| | |
|---|---|
| *A61B 18/14* | (2006.01) |
| *A61B 18/10* | (2006.01) |
| *A61B 18/00* | (2006.01) |
| *A61B 34/30* | (2016.01) |
| *A61B 90/00* | (2016.01) |

(52) U.S. Cl.
CPC .......... *A61B 18/1492* (2013.01); *A61B 34/30* (2016.02); *A61B 2018/0072* (2013.01); *A61B 2018/00351* (2013.01); *A61B 2018/00357* (2013.01); *A61B 2018/00375* (2013.01); *A61B 2018/00577* (2013.01); *A61B 2018/00702* (2013.01); *A61B 2018/00767* (2013.01); *A61B 2018/00875* (2013.01); *A61B 2034/301* (2016.02); *A61B 2090/065* (2016.02); *A61B 2218/002* (2013.01)

(58) Field of Classification Search
CPC .... A61B 2018/00738; A61B 2017/003; A61B 2018/00702; A61B 18/00; A61B 2019/464; A61B 17/00234; A61B 2018/00648; A61B 2017/00292; A61B 2018/00773; A61N 1/05
See application file for complete search history.

(56) References Cited

U.S. PATENT DOCUMENTS

| | | |
|---|---|---|
| 5,423,811 A | 6/1995 | Imran et al. |
| 5,437,662 A | 8/1995 | Nardella |
| 5,454,370 A | 10/1995 | Avitall |
| 5,486,161 A | 1/1996 | Lax et al. |
| 5,540,681 A | 7/1996 | Strul et al. |
| 5,542,915 A | 8/1996 | Edwards et al. |
| 5,542,916 A | 8/1996 | Hirsch et al. |
| 5,599,294 A | 2/1997 | Edwards et al. |
| 5,688,267 A | 11/1997 | Panescu et al. |
| 5,735,846 A | 4/1998 | Panescu et al. |
| 5,843,075 A | 12/1998 | Taylor |
| 5,860,974 A | 1/1999 | Abele |
| 5,868,737 A | 2/1999 | Taylor et al. |
| 5,871,523 A | 2/1999 | Fleischman et al. |
| 5,971,980 A | 10/1999 | Sherman |
| 6,001,093 A | 12/1999 | Swanson et al. |
| 6,013,074 A | 1/2000 | Taylor |
| 6,030,382 A | 2/2000 | Fleischman et al. |
| 6,039,731 A | 3/2000 | Taylor et al. |
| 6,052,618 A | 4/2000 | Dahlke et al. |
| 6,056,745 A | 5/2000 | Panescu et al. |
| 6,129,724 A | 10/2000 | Fleischman et al. |
| 6,287,306 B1 | 9/2001 | Kroll et al. |
| 6,322,558 B1 | 11/2001 | Taylor et al. |
| 6,447,506 B1 | 9/2002 | Swanson et al. |
| 6,488,678 B2 | 12/2002 | Sherman |
| 6,517,536 B2 | 2/2003 | Hooven et al. |
| 6,584,360 B2 | 6/2003 | Franciscelli et al. |
| 6,652,515 B1 * | 11/2003 | Maguire ............... A61B 18/00 606/41 |
| 6,696,844 B2 | 2/2004 | Wong et al. |
| 6,989,010 B2 | 1/2006 | Francischelli et al. |
| 7,048,734 B1 | 5/2006 | Fleischman et al. |
| 7,137,980 B2 | 11/2006 | Buysse et al. |
| 7,151,964 B2 | 12/2006 | Desai et al. |
| 7,163,534 B2 | 1/2007 | Brucker et al. |
| 7,282,049 B2 | 10/2007 | Orszulak et al. |
| 7,306,593 B2 | 12/2007 | Keidar et al. |
| RE40,388 E | 6/2008 | Gines |
| 7,465,300 B2 | 12/2008 | Arless et al. |
| 7,608,072 B2 | 10/2009 | Swanson |
| 7,850,685 B2 | 12/2010 | Kunis et al. |
| 8,075,498 B2 | 12/2011 | Leo et al. |
| 8,182,433 B2 | 5/2012 | Leo et al. |
| 8,409,191 B2 | 4/2013 | Avitall |
| 8,437,832 B2 | 5/2013 | Govari et al. |
| 8,583,220 B2 | 11/2013 | Schwartz |
| 8,641,705 B2 | 2/2014 | Leo et al. |
| 8,926,604 B2 | 1/2015 | Govari et al. |
| 9,149,327 B2 | 10/2015 | Lambert et al. |
| 2004/0147920 A1 | 7/2004 | Keidar |
| 2005/0177151 A1 | 8/2005 | Coen et al. |
| 2005/0256522 A1 | 11/2005 | Francischelli et al. |
| 2006/0095030 A1 | 5/2006 | Avitall et al. |
| 2006/0200049 A1 | 9/2006 | Leo et al. |
| 2007/0060847 A1 | 3/2007 | Leo et al. |
| 2007/0093806 A1 | 4/2007 | Desai |
| 2007/0208333 A1 | 9/2007 | Uchida et al. |
| 2007/0219546 A1 | 9/2007 | Mody et al. |
| 2008/0009750 A1 | 1/2008 | Aeby et al. |
| 2008/0097220 A1 | 4/2008 | Lieber et al. |
| 2008/0147057 A1 | 6/2008 | Eisele |
| 2008/0161793 A1 | 7/2008 | Wang et al. |
| 2008/0275440 A1 | 11/2008 | Kratoska et al. |
| 2008/0294144 A1 | 11/2008 | Leo et al. |
| 2008/0300588 A1 | 12/2008 | Groth et al. |
| 2009/0138007 A1 | 5/2009 | Govari |
| 2009/0177111 A1 | 7/2009 | Miller et al. |
| 2009/0306643 A1 | 12/2009 | Pappone et al. |
| 2009/0306650 A1 | 12/2009 | Govari et al. |
| 2010/0069921 A1 | 3/2010 | Miller et al. |
| 2010/0041986 A1 | 7/2010 | Nguyen |
| 2010/0168738 A1 | 7/2010 | Schneider et al. |
| 2010/0185186 A1 | 7/2010 | Longoria |
| 2010/0298825 A1 | 11/2010 | Slizynski et al. |
| 2010/0298826 A1 | 11/2010 | Leo et al. |
| 2011/0152856 A1 | 1/2011 | Govari et al. |
| 2011/0144524 A1 | 6/2011 | Fish et al. |
| 2012/0209260 A1 | 8/2012 | Lambert et al. |
| 2016/0095653 A1 | 4/2016 | Lambert et al. |

FOREIGN PATENT DOCUMENTS

| | | |
|---|---|---|
| EP | 2047797 A2 | 4/2009 |
| EP | 2064990 | 6/2009 |
| EP | 2047797 A3 | 9/2009 |
| EP | 2248480 | 11/2010 |
| JP | 2007-54622 | 3/2007 |
| JP | 2009505708 A | 2/2009 |
| JP | 2010107727 | 5/2010 |
| WO | 2007001981 | 1/2007 |
| WO | 2007023407 A1 | 3/2007 |
| WO | 2007050960 | 5/2007 |
| WO | 2007109171 | 9/2007 |
| WO | 2008045958 | 4/2008 |
| WO | 2008063195 | 5/2008 |

OTHER PUBLICATIONS

Calkins et al., "HRS/EHRA/ECAS expert Consensus statement on catheter and surgical ablation of atrial fibrillation: recommendations for personnel, policy, procedures and follow-up" A report of the Heart Rhythm Society (HRS) Task force on catheter and surgical ablation of the atrial fibrillation, Europace (2007), vol. 8, pp. 335-379.

Calkins et al., "2012 HRS/EHRA/ECAS expert Consensus statement on catheter and surgical ablation of atrial fibrillation: recommendations for patient selection, procedural techniques, patient management and follow-up, definitions, endpoints and research trial design", J. Interv Card Electrophysiol, Mar. 1, 2012, pp. 1-87.

Pappone et al., "Non-fluoroscopic mapping a s aguide for atrial ablation: current status and expectations for the future", European

(56) References Cited

OTHER PUBLICATIONS

Hearth Journal Supplements, vol. 9, Supplement 1, pp. 1136-1145, Dec. 2007.
Yokoyama et al., Novel contact force sensor incorporated in irrigated radiofrequency ablation catheter predicts lesion size and incidence of steam pop and thrombus: Circulation Arrhythmia and Electrophysiology, Dec. 2008, Dallas, TX.
Acker, et al., "Featured Poster Session", Heart Rhythm, vol. 6, No. 5, May 13, 2009, pp. S95-S120.
Kuck, "First clinical data on catheter contact force—impact on safety and effectiveness, (power point presentation)" St. Georg Hospital in Hamburg, Germany, presented May 2009.
Seiler et al., "Steam pops during irrigated radiofrequency ablation: feasibility of impedance monitoring for prevention", Jul. 2008).
Topp et al., "Saline-linked surface radiofrequency ablation: factors affecting steam popping and depth of injury in the pig liver", Apr. 2004, St. Louis, Missouri.
Huang et al., "Catheter ablation of cardiac arrhythmias", Catheter ablation of cardiac arrhythmia, Chapter 1, Mar. 2006, pp. 1-20.
Watanabe et al., "Cooled-tip ablation results in increased radiofrequency power delivery and lesion size in the canine heart: importance of catheter-tip temperature monitoring for prevention of popping and impedance rise", Journal of linventional cardiac electrophysiology, vol. 6, No. 2, Abstract, Feb. 2002.
Kuck, "Importance of catheter contact force and stability in radiofrequency catheter ablation, (power point presentation)" St. Georg Hospital in Hamburg, Germany, May 14, 2008.
Japanese Patent Office, Notification of Reasons for Rejection, issued in counterpart JP application 2017-239093. dated May 14, 2019.

\* cited by examiner

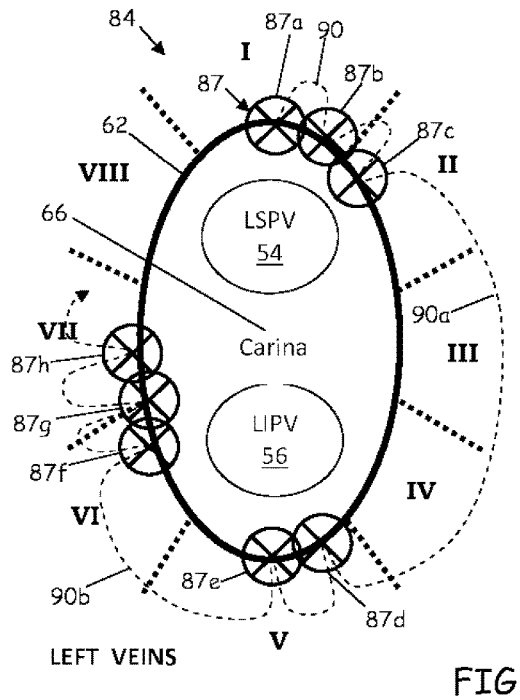
LEFT VEINS
FIG. 7A
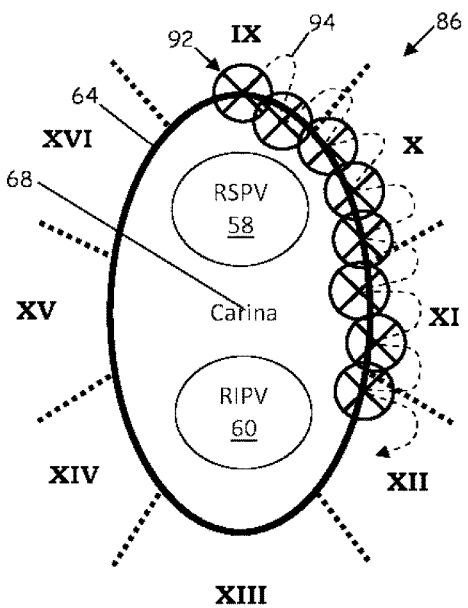
RIGHT VEINS
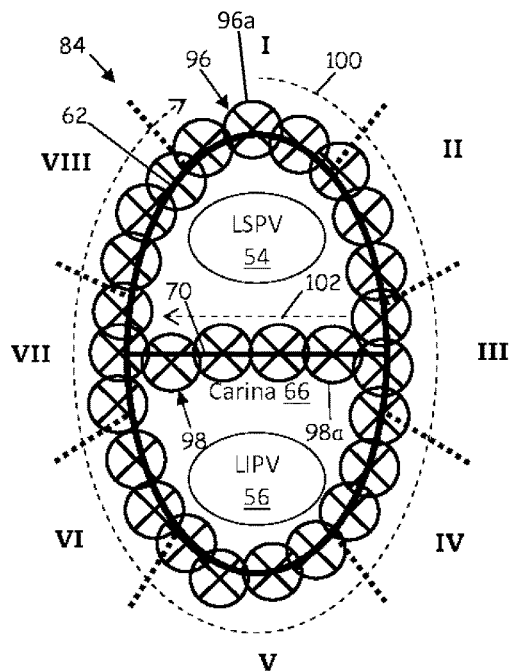
FIG. 7B
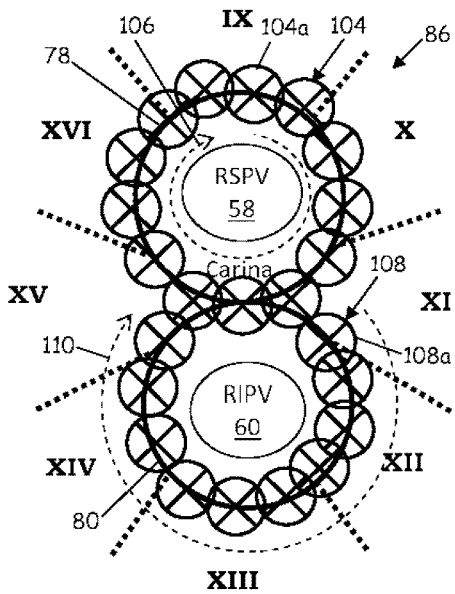
FIG. 7C

PREDICTION OF ATRIAL WALL ELECTRICAL RECONNECTION BASED ON CONTACT FORCE MEASURED DURING RF ABLATION

CROSS-REFERENCE TO RELATED APPLICATIONS

This is a divisional of U.S. patent application Ser. No. 14/876,786 filed 5 Oct. 2015 (the '786 application), which is a continuation of U.S. patent application Ser. No. 13/337,896, filed 27 Dec. 2011 (the '896 application), now U.S. Pat. No. 9,149,327, issued 6 Oct. 2015, which claims the benefit of U.S. provisional patent application Nos. 61/427,423 (the '423 application) and 61/427,425 (the '425 application), both filed on 27 Dec. 2010. The '786, '896, '423, and '425 applications are hereby incorporated by reference in their entirety as though fully set forth herein.

BACKGROUND a. Field

The field of the invention relates generally to the treatment of organic tissues using ablation therapy, and more specifically to the prediction and display of lesion sizes using catheter-based contact ablation delivery systems.

b. Background Art

Atrial fibrillation is a common cardiac arrhythmia involving the two upper chambers (atria) of the heart. In atrial fibrillation, disorganized electrical impulses that originate in the atria and pulmonary veins overwhelm the normal electrical impulses generated by the sinoatrial node, leading to conduction of irregular impulses to the ventricles that generate the heartbeat. Atrial fibrillation can result in poor contraction of the atria that can cause blood to recirculate in the atria and form clots. Thus, individuals with atrial fibrillation have a significantly increased risk of stroke. Atrial fibrillation can also lead to congestive heart failure or, in extreme cases, death.

Common treatments for atrial fibrillation include medications or synchronized electrical cardioversion that convert atrial fibrillation to a normal heart rhythm. Surgical-based therapies have also been developed for individuals who are unresponsive to or suffer serious side effects from more conventional treatments. The surgical techniques include making incisions in the right and left atria to block propagation of the abnormal electrical impulse around the atrial-chamber.

Catheter-based contact ablation techniques have evolved as a minimally invasive alternative to surgical-based techniques, and also as an alternative for individuals who are unresponsive to or suffer serious side effects from more conventional treatments (e.g., medications). Contact ablation techniques involve the ablation of groups of cells near the pulmonary veins where atrial fibrillation is believed to originate, or the creation of extensive lesions to break down the electrical pathways from the pulmonary veins located on the posterior wall of the left atrium. Methods of energy delivery include radiofrequency, microwave, cryotherapy, laser, and high intensity ultrasound. The contacting probe is placed into the heart via a catheter that enters veins in the groin or neck and is routed to the heart, thus negating the need for an incision in the heart wall from the outside. The probe is then placed in contact with the posterior wall of the left atrium and energized to locally ablate the tissue and electrically isolate the pulmonary veins from the left atrium. The advantages of catheter-based contact ablation techniques have been recognized to include a minimally invasive surgical access, thus reducing risks of infection, and reduced recuperation times.

Where complete electrical isolation is desired, the objective of the contact ablation technique is to form a continuous "ablation line" or "isolation line" of ablated tissue between the left atrium and the pulmonary veins. Two different approaches for achieving an isolation line have been developed: point contact ablation where the energy delivery is from a head end of the contacting probe generally in line with a longitudinal axis of the contacting probe; and linear contact ablation where the energy delivery is from a side of the contacting probe and generally transverse to the longitudinal axis of the contacting probe.

A concern with catheter-based contact ablation techniques is the post-operative recurrence of atrial fibrillation, believed to be caused by electrical reconnection of pulmonary veins across the isolation line. The sites along the isolation line where this type of electrical reconnection occurs are referred to as "isolation gaps" or simply "gaps." Gaps can occur due to suboptimal catheter contact force during ablation for either point contact ablation or linear contact ablation techniques. The left anterior wall is often a difficult area to achieve stable contact during pulmonary vein isolation resulting in higher incidence of local isolation gaps.

One approach to identifying or predicting possible isolation gaps has been to make electrical continuity measurements across the isolation line after the isolation line has been created. While this approach may work in some cases for linear contact ablation techniques, it is generally not effective for point contact ablation techniques because it requires too much time and too many continuity measurements in order to establish a relatively high confidence in the ability to predict whether there will or will not be isolation gaps as a result of incomplete lesion formations during the ablation process of creating the isolation. In addition, it has been found that intra-operative continuity measurements of the isolation line may not be an accurate predictor of the recurrence of atrial fibrillation as the tissue properties of the lesion just after ablation can change over time and may not be representative of the final lesions associated with the isolation line.

The predictability of lesion formation in the context of point contact ablation techniques has been enhanced with the advent of force sensing ablation catheters. The ability to incorporate the contact forces utilized in point-to-point ablation procedures has led to new systems and processes directed to the prediction of ablation size. U.S. patent application publication no. 2010/0298826 to Leo et al. (Leo), assigned to the assignee of the instant application, discloses the use of a force-time integral for real time estimation of lesion size in catheter-based ablation systems.

Further improvements in the application of force sensing catheter-based contact ablation devices and methods to mitigate the occurrence of electrical reconnection across isolation lines after ablation treatments for atrial fibrillation would be a useful and welcomed development.

BRIEF SUMMARY

A device and method for prediction of successful isolation and/or the occurrence of gap formation in the contact of catheter-based point contact ablation techniques is presented. In one embodiment, the size of a lesion is predicted on the basis of the contact force between the ablation head and a target tissue, an energization parameter applied to the ablation head during contact, and the time duration of the ablation. In another aspect of the invention, the integrity of the isolation line can be enhanced as well as predicted by tracking and quantifying the sequential nature (sequence in time and space) of the ablation line formation. The ability to better predict the temporal and spatial vicinity of a pair of consecutively formed lesions without the need for repeated post-ablation measurement is then utilized by various embodiments of the invention to dynamically determine aspects of subsequent contact point lesion to create a more effective isolation line.

With respect to the prediction of lesion size, various embodiments of the invention predict the lesion size based on a quantity referred to herein as the "lesion size index," or "LSI." The LSI is a parameter that can be used to evaluate the lesion size during an ablation in real time. More specific forms of the lesion size index include a "lesion width index" (LWI) for estimating the maximum width or diameter of a lesion, a "lesion depth index" (LDI) for estimating the maximum and/or effective depth of the lesion, and the "lesion volume index" (LVI) for estimating the total volume of the lesion.

In one embodiment, the LSI is derived from a mathematical expression that incorporates a contact force F between the ablation head and the target tissue, an energization parameter E applied to target the tissue (e.g., power, current or voltage), and a duration time t of the energization. These indexes are based on an empirical model developed from a series of experiments where lesion sizes were formed on the beating hearts of canines and the lesions subsequently measured.

The LSI represents an improvement over the force-time integral in several respects. For instance, the LSI incorporates the energization parameter E directly. Also, the LSI is based on a model that utilizes both a joule heating component (i.e., heating by the passage of electrical current) and a diffusive heating component. The LSI model can also account for more subtle, non-linear characteristics of lesion formation, such as the delay between the variation of force and/or current and the change of lesion growth rate due to thermal latency, and the discovery that lesions rapidly grow to a certain depth (typically about 3 mm), beyond which the depth parameter continues to grow at a slower rate. Furthermore, the LSI model can account for the different results from different energizations. For example, an increase in the energization and/or contact force will cause the growth rate of the lesion to increase. A moderate drop in energization and/or contact force causes the growth rate of lesions to slow, while a dramatic drop in energization and/or contact force causes the growth rate to stop altogether. Embodiments of the LSI model can account for these various characteristics of lesion formation. Thus, the combination of the aforementioned aspects of the LSI enable a robust and refined prediction of lesion size.

With respect to the sequential aspects of line formation, the temporal and spatial vicinity of two consecutive lesions has been found to be a factor in the quality of isolation line continuity. Spatial vicinity (i.e., formation of adjacent lesions in sequence) is advantageous because of the limited reproducibility of the catheter positioning systems and limitations with respect to catheter maneuverability. Temporal vicinity (i.e., formation of the lesions in a time efficient manner) is also advantageous because, within approximately a minute after ablation, edema is formed. The onset of edema can vitiate the formation of lesions in the adjacent area.

Accordingly, various embodiments of the invention track and quantify the sequential characteristics of the isolation line formed by the ablation process using a parameter herein referred to as the "jump index," or "JI." In one embodiment, a zoned-based accounting of the jump index is utilized. For zone-based accounting, the isolation line to be formed is divided into a series of ablation zones. The jump index JI can be a cumulative sum of the number of ablation zones that are passed over or "jumped" between two consecutive but non-adjacent lesion formations during the formation of the isolation line. That is, if a pair of lesions consecutively formed are centered within ablation zones that are adjacent each other, the jump index JI is not incremented because no ablation zones were passed over between the formation of the consecutive lesions. However, if two consecutively formed lesions are in non-adjacent zones, the JI is incremented by the number of ablation zones that were passed over between the two ablation sites. Treatment of the carina between two ipsilateral veins before a full isolation around the veins is completed is also considered a jump. The incrementing of the jump index JI is tracked until at least one lesion has been formed in all designated zones of the desired isolation line, at which time the incrementing of the JI ceases.

In another embodiment, a distance-based detection of jump is utilized. With distance-based methods, a "jump" occurs whenever the distance between consecutively formed lesions along a desired isolation line exceeds a predetermined arc length. Here, the incrementing of the jump index can remain active, for example, until the maximum arc length between any two lesions is less than the predetermined arc length.

Accumulation of a low jump index JI during the formation of an isolation line results in a statistically significant increase in the success of the isolation line long term (3 months or more). That is, a low JI results in an enhanced, statistically significant chance that no post-operative gaps will form, at least within the first 3 months after ablation.

The jump index JI not only demonstrates the superior effectiveness of constructing an isolation line in a substantially consecutive manner, but can also be implemented as a predictor of gap formation in procedures where isolation line formation did not occur in a substantially sequential manner. Accordingly, in certain embodiments, the probability of gap prediction is based on 1) the lesion size index LSI or the force-time integral FTI and 2) the jump index JI. The LSI and/or FTI is believed to be an indicator of lesion transmurality, and the jump index JI is believed to be an indicator of the continuity of the isolation line.

In various embodiments, a method of forming an isolation line in a region of a human heart, is described. The method comprises providing an elongate flexible catheter adapted to be introduced into a patient during a medical procedure, the catheter including a distal portion having an ablation head operatively coupled with a force sensor, a position sensing device and a control system. The control system can include a processor operatively coupled with the force sensor, the position sensing device and a receiving device (such as a robotic manipulator or a display), the processor having access to a storage medium that contains programming instructions to be executed by the processor. In one embodiment, the programming instructions include:

determining an actual location of a first lesion of the isolation line;

calculating a desired location for a second lesion, the desired location of the second lesion being proximate to and based on the actual location of the first lesion;

generating an instruction to position the ablation head at the desired location of the second lesion; and sending the instruction to position the ablation head at the desired location of the second lesion to the receiving device.

The method can also comprise providing an energy source operatively coupled with an energization parameter measuring device, the energy source also being operatively coupled with the ablation head and the processor. Additional programming instructions contained on the storage medium to be executed by the processor can include:

energizing the ablation head with the energy source for formation of the second lesion;

acquiring position data from the position sensing device during formation of the second lesion;

acquiring force data from the force sensor during formation of the second lesion;

acquiring energization parameter data from the energization parameter measuring device during formation of the second lesion; and acquiring duration time data for formation of the second lesion.

In another embodiment of the invention, the programming instructions can further comprise:

determining an actual location of the second lesion from the position data acquired during formation of the second lesion, calculating a desired location for a third lesion, the desired location of the third lesion being proximate to and based on the actual location of the second lesion;

generating an instruction to position the ablation head at the desired location of the third lesion;

sending to the receiving device the instruction to position the ablation head at the desired location of the third lesion; and calculating the desired location for the third lesion based on the estimated size of the second lesion.

The desired location of the second lesion can be sufficiently close to the first lesion for continuity between the first and second lesions if the second lesion is formed at the desired location, and, in some embodiments, the second lesion physically overlaps the first lesion if the second lesion is formed at the desired location.

In another embodiment of the invention, a method for automatically controlling an ablation catheter comprises providing an elongate flexible catheter, the catheter including a distal portion having an ablation head and a force sensor and operatively coupled with an energy source. Instructions are provided for introducing the catheter into a patient during a medical procedure and guiding the distal portion of the catheter so the ablation head of the catheter is exerted against a first target tissue location. The ablation head is automatically energized with the energy source over a period of time while the ablation head is exerted against the first target tissue location. A sequence of energization parameters (e.g., electrical current) can also be measured with the energization parameter measuring device, as well as a sequence of contact forces with the force sensor, while the ablation head is energized, the contact forces being in reaction to the ablation head exerted against the target tissue. A lesion size can be automatically determined based on the sequence of contact forces and the sequence of the energization parameters over the selected period of time. In one embodiment, the determination of lesion size includes determining a joule heating component and a diffusive heating component. Also, control information can be automatically generated based on the lesion size for use in guiding the ablation head to a second and subsequent target tissue location.

In another embodiment, a method for automatically controlling an ablation catheter includes providing an elongate flexible catheter with a distal portion having an ablation head operatively coupled with an energy source and a position sensing device, and also providing instructions for introducing the catheter into a patient during a medical procedure and guiding the distal portion of the catheter so the ablation head of the catheter is exerted against a first target tissue location. The ablation head can be automatically energized with the energy source over a period of time while the ablation head is exerted against the first target tissue location. A sequence of locations of the distal portion of the elongate flexible catheter can then be measured with the position sensing device while the ablation head is energized. A location of a lesion created during the energizing of the ablation head can be automatically inferred from the sequence of locations, and control information automatically generated based on the location of the lesion for use in guiding the ablation head to a second and subsequent target tissue location. In addition, this method can further comprise measuring a sequence of contact forces with the force sensor, and measuring a sequence of energization parameters with the energization parameter measuring device, all while the ablation head is energized. A lesion size can then be determined based on the sequence of contact forces and the sequence of the energization parameters measured over the period of time. Control information can be automatically generated based on the lesion size, for use in guiding the ablation head to the second and subsequent target tissue location.

In another embodiment, a method for determining the continuity of an isolation line formed by point contact ablation in a region of the human heart is disclosed. The method includes providing an elongate flexible catheter, the catheter including a distal portion having an ablation head operatively coupled with an energy source, a force sensor and a position sensing device, the energy source, the force sensor and the position sensing device being operatively coupled with a processor. A processor can be configured to:

provide instructions for forming a plurality of lesions substantially along a desired ablation line with the ablation head;

sense the location of each of the plurality of lesions with the position sensing device during the forming of the plurality of lesions;

determine if a jump occurred between each consecutively formed pair of lesions of the plurality of lesions, the jump being defined by a predetermined criteria of spatial separation between the lesions of the consecutively formed pairs of lesions, and increment a jump index for each jump detected in the formation of the plurality of lesions.

A probability of gap formation along the isolation line can also be determined based on the jump index and the force data. In one embodiment, the predetermined criteria for determining if a jump occurred is based on a zoned accounting method wherein the isolation line is divided into adjacent zones and the jump is established when consecutively formed lesions are created in nonadjacent zones.

In another aspect of the invention, a method for predicting the depth of lesions formed during RF ablation therapy is developed and presented based on the force-time integral (FTI). In one embodiment, lesion depth predictions utilizing the FTI are based on two parameters: (1) the contact force between the RF ablation head and the target tissue, and (2) the power delivered to the RF ablation head. In still another aspect of the invention, a relationship between contact force and the formation of gaps in the isolation line is established. A prospective study was performed for an evaluation of electrical reconnections at three months after the ablation procedure. The objective of the study was to identify parameters correlating to gaps in the isolation line and to predict the likelihood of failure of the isolation treatment.

The foregoing and other aspects, features, details, utilities, and advantages of the present disclosure will be apparent from reading the following description and claims, and from reviewing the accompanying drawings.

BRIEF DESCRIPTION OF THE DRAWINGS

FIGS. 7A through 7C depict a zone accounting method for tracking the jump index in embodiments of the invention;

DETAILED DESCRIPTION OF EMBODIMENTS

Figure 1:
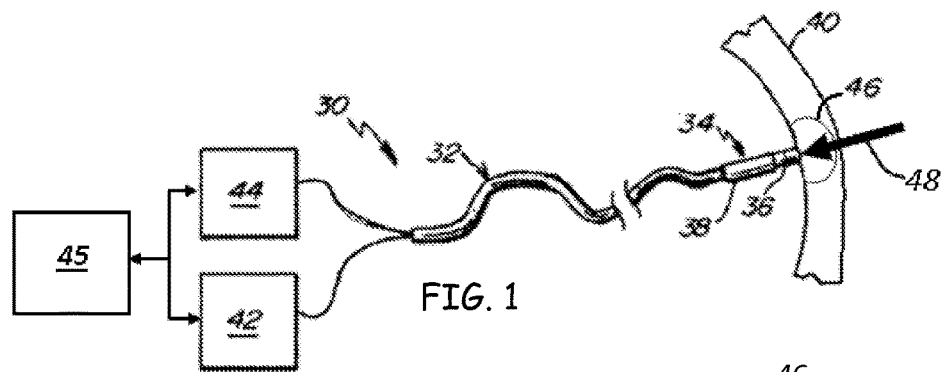
FIG. 1 depicts a schematic of a contact ablation system in an embodiment of the invention.

Referring to FIG. 1, a contact ablation system 30 is depicted in an embodiment of the invention. The contact ablation system 30 includes a catheter 32 having a distal portion 34 comprising an ablation head 36 operatively coupled with a force sensor 38, the ablation head 36 arranged for contact with a target tissue 40. The catheter 32 is operatively coupled with a power source 42 that provides and measures the delivered energy to the ablation head 36. A measurement device 44 is also depicted, capable of sourcing the force sensor 38 and measuring an output signal from the force sensor 38. The contact ablation system 30 can also include a central controller 45 such as a computer or microprocessor operatively coupled with the power source 42 and the measurement device 44 for control thereof and for processing information received therefrom.

In operation, the ablation head 36 is brought into contact with the target tissue 40 and energized to create a lesion 46 on and within the target tissue 40. The force sensor 38 is configured to generate an output from which a magnitude of a contact force vector 48 can be inferred. Generally, the contact force is time-variant, particularly when the target tissue 40 is subject to motion (e.g., the wall of a beating heart). The energy flow (e.g., current or power) through the ablation head 36 can also be time variant, as the energy flow may depend on the contact resistance between the ablation head 36 and the target tissue 40, which in turn can vary with the contact force and the changing properties of the lesion 46 during ablation.

Figure 2:
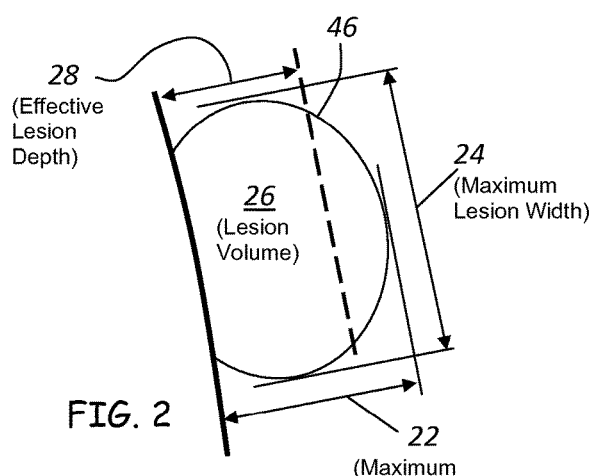
FIG. 2 depicts parameters of the point contact ablation lesion of FIG. 1.

Referring to FIG. 2, typical characteristics of the lesion 46 are depicted. The lesion 46 can be 15 characterized as having a maximum depth 22, a maximum width 24 and a volume 26. An effective depth 28 can also be characterized as the maximum depth 22 divided by the square root of two (√2).

Various embodiments of the invention implement a "force-time integral" (FTI), broadly defined herein as a measured quantity that involves the measurement of force over time. The force-time integral can be defined one of several ways, all involving the measurement of force over time. One example of a force-time integral is, of course, the numerical integration of the force over time (FOT):

$$FOT = \int F(t)dt \qquad \text{Eqn. (1)}$$

where F(t) is the contact force measured over time between a target tissue and a distal portion of an ablation head. The parameter t designates time, indicating that the contact force can be time variant.

The force-time integral can also be expressed a force-time product (FTP), given by $$FTP = \overline{F} \cdot \Delta t \qquad \text{Eqn. (2)}$$

where $\overline{F}$ is a representative value of F(t) over a time period Δt.

Another expression of a force-time integral comprises a force-energization over time (FEOT) integral or a force-energization-time product (FETP), given respectively as $$FEOT = \int F(t)E(t)dt \qquad \text{Eqn. (3)}$$

$$FETP = \overline{F} \cdot \overline{E} \cdot \Delta t \qquad \text{Eqn. (4)}$$

where E(t) is the measured energization indicative of the energy flow delivered to the ablation head (e.g., power or electrical current) and $\overline{E}$ is a representative value of the measured energization E(t) over the time period Δt (for example a time-averaged energization value). The measured energization E(t) can also be time-variant, as noted above. The force-time-energization product (FETP) can include combinations of the above parameters, for example:

$$FETP = \overline{E} \int F(t)dt \qquad \text{Eqn. (5)}$$

$$FETP = \overline{F} \int E(t)dt \qquad \text{Eqn. (6)}$$

In another embodiment, a normalized force over time (NFOT) integration that is normalized with respect to the energization levels can also be implemented:

$$NFOT = \frac{\int F(t)E(t)dt}{\int E(t)dt} \cdot \Delta t \qquad \text{Eqn. (7)}$$

Such an approach may be useful for enhanced accuracy where only FOT or FTP calibrations are available.

It is further noted that with respect to the present invention the measurement of "force" per se is not necessary to infer or derive a force-time integral. Although force and strain or pressure may not be equivalent in other contexts, other parameters that have a relationship with force (e.g., strain, pressure) can be substituted for the force component of the force-time integral in the present invention and still reliably predict lesion size. Likewise, it is understood that other references to "force" herein (including, but not limited to, force sensor, force signal, force conversion, force set point, force interval, force values, force measurement, force level, force limits, contact force and reaction force) are intended to be broadly construed to include other parameters such as pressure and strain that have a relationship with force.

Patients with paroxysmal atrial fibrillation received pulmonary vein (PV) isolation in accordance with standard ablation procedures using an irrigated RF ablation catheter that provides tip-to-tissue contact force information (TACTICATH, Endosense, Switzerland). The operator was blinded to contact force, which was recorded for later analysis. Pulmonary vein antra were each divided into 8 segments of interest. For each ablation, the catheter position, contact force, RF power and the force-time integral (FTI) were collected. The FTI is a useful parameter for expressing the accumulated energy delivered in an ablation (i.e. the energy delivered during the formation of a lesion), with unstable contact resulting in low FTI.

The initial application of RF at each segment was separately analyzed to give insight into early tissue changes with focus on low FTI. Patients underwent a $2^{nd}$ interventional diagnostic procedure at three months to evaluate gap occurrence in each segment of interest for each pulmonary vein. Incidence of gaps per segment of interest at three months was correlated with contact force and FTI during the pulmonary vein isolation procedure, and a method for gap prediction developed based on these parameters.

Twenty-seven patients having an age span of 58+/−11 years (nineteen males and eight females) were treated at two centers by nine different operators. Thirteen patients were subject to a three month interventional follow up, of which five gaps on the left anterior wall were detected. There was no measurable difference in contact force for sections with gap or without gap (13.4±4.7 gmf vs. 13.1±7.5 gmf, p=0.2727, where "gmf" is the force equivalent of the weight of one gram at standard gravity). However, for the first RF application at each segment of interest, the FTI was significantly lower in segments with gaps than with no gap (79.0±68.2 gmf-sec vs. 364.8±568.4 gmf-sec, p=0.0006). Probability for gap occurrence at the left atrial wall increases by 18% for every first RF application where the FTI is less than 250 gmf-sec per segment.

Combining gap probability per segment of interest provides a method for predicting the likelihood of reconnection at the left atrium wall per patient. The method is able to discriminate between patients with gaps versus patients with no gaps at the left atrium wall (45% vs 24%, p=0.0015).

The general methodology is as follows:
Assumptions
  First ablation is determinant, too low (<250) FTI induces an edema and cannot be catched again.
  2 ablations are required to isolate a segment.
  Each bad event induces a certain probability of getting a gap.
  The probability to have a gap at the patient level is the product of the probability to have a gap at the segment level.
Determination of the probability of success
  Counting the number of ablation within the 2 first for each position where FTI has been lower than 250 gmf-sec (defined as a "bad event").
  the probability that such an event is followed by a gap is $p_{position}$=(#ablation |FTI<250 gmf-sec. at position i & gap at this position)/(#ablation |FTI<250 gmf-sec at position i)
  For each position the probability of success after such a bad event occurs is $P_{success\_position}=1-p_{position}$
Computing the predictive probability for each patient.
  Counting for a patient when a "bad ablation" has been done within the 2 first ablations for each position: $N_{bad}$
  Probability of success for a certain number of position is $P_{success}=(P_{success\_position})^{Nbad}$ On the left atrium wall, a low initial FTI is a predictive parameter for early gap 15 occurrence following pulmonary vein isolation. The probability of gap occurrence can be quantified. This allows a prediction of the probability of success per patient already during pulmonary vein isolation and has the potential to adapt ablation strategy during the procedure. In one embodiment of the invention, lesion depth predictions were correlated from ablation studies, based on pre-clinical ablation studies involving a total of 31 animals and 218 measures. A lesion depth (D) was found to correlate a general data form as follows $$D=(A1 \cdot F2+A2 \cdot F+A3) \cdot (B1-P2+B2 \cdot P) \qquad \text{Eq. (8)}$$

where F is contact force (e.g., gmf), P is power delivered to the ablation head (e.g., watts), and A1, A2, A3 and B1, B2 are coefficients based on curve fits to the animal study data. A "gmf" is the force equivalent to the weight of 1 gram of mass at standard gravity.

Figure 3:
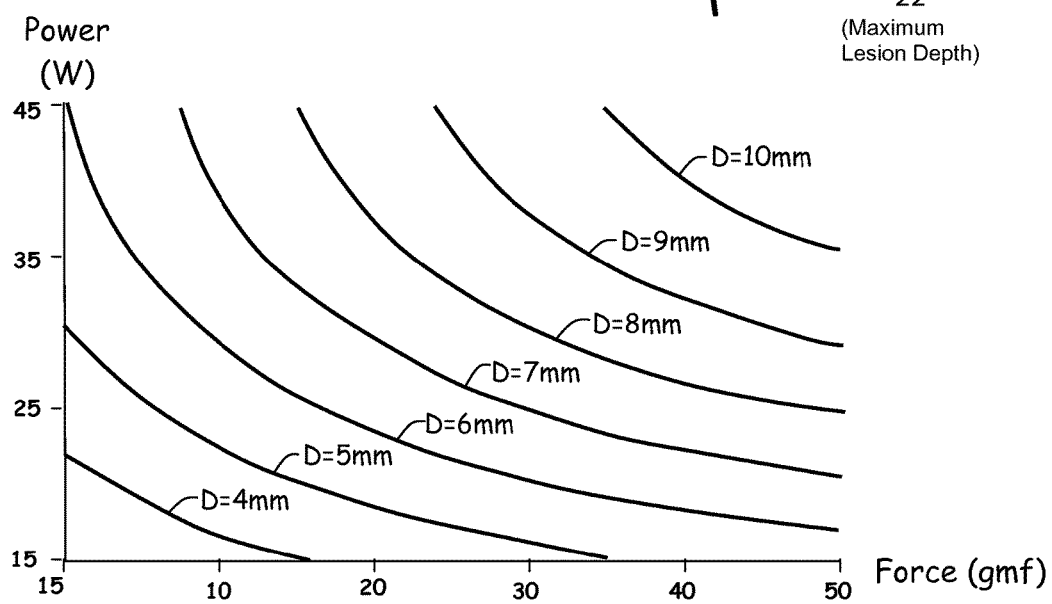
FIG. 3 is a graph of lesion depths as a function of RF ablation power and contact force in an embodiment of the invention.
Figure 4:
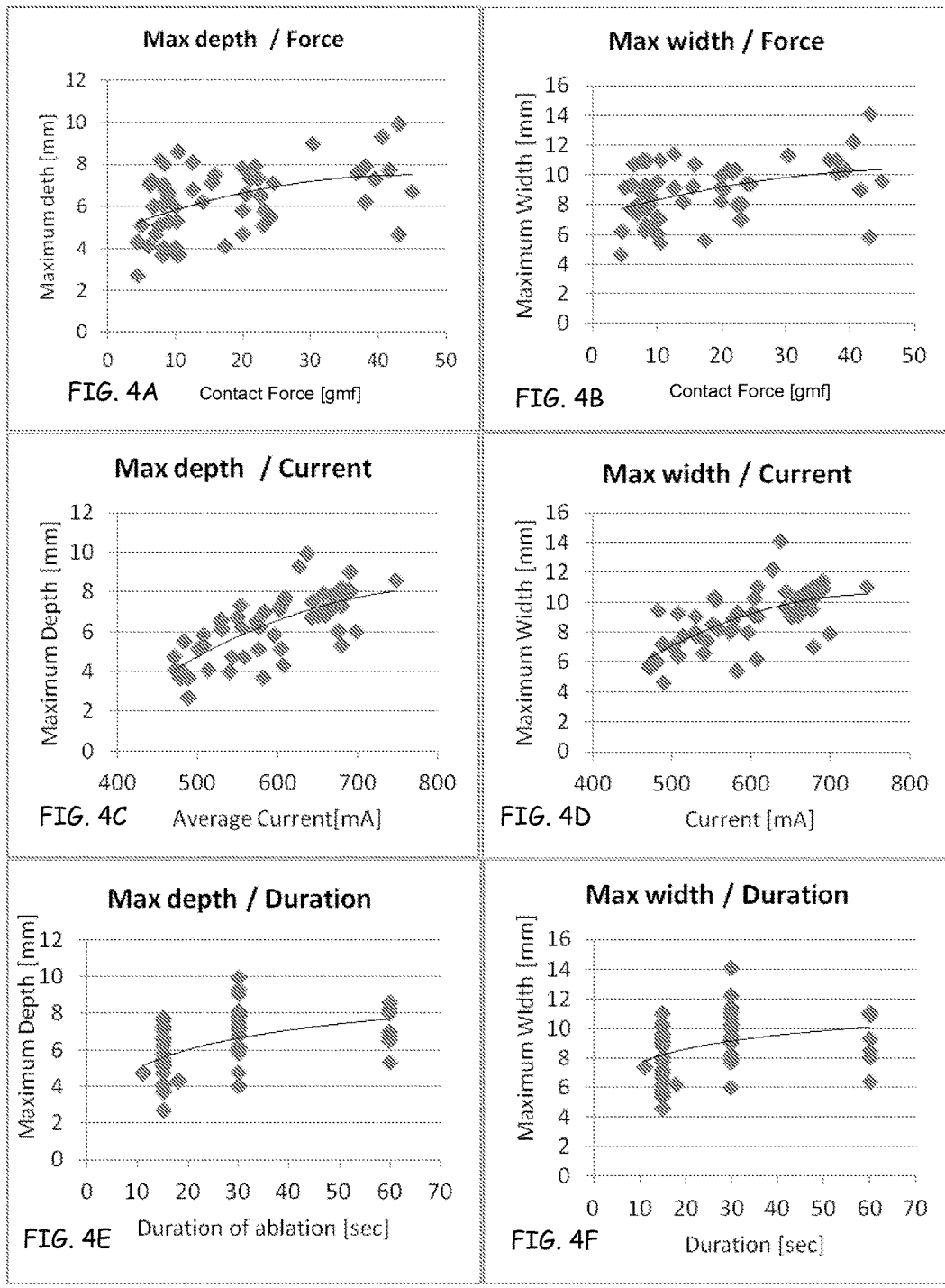
FIGS. 4A through 4F are graphical representations of data used in embodiments of the invention.

An example and non-limiting graph predicting lesion depth D is presented at FIG. 3. The predictions take the form of Eq. (8) and are based on three sets of data from ablation studies on animals involving a total of 31 animals and 218 measures. The least-squares values of the coefficients A1, A2, A3 and B1, B2 for the curve fits presented in FIG. 3 are:
  A1=−0.29E-05 mm/gmf$^2$
  A2=1.41E-02 mm/gmf
  A3=0.559 mm
  B1=−3.81E-03 W$^2$
  B2=0.409

In another embodiment of the invention, a lesion size index (LSI) is related to the contact force F between the ablation head 36 and the target tissue 40, an energization parameter E applied to target the tissue (e.g., power, voltage, current), and the duration time t of the ablation. The effect of these parameters have been modelled and correlated with ablation data from numerous clinical studies to arrive at an equation set based on the model. The LSI can thus be expressed as a retrospective equation or set of equations that can be programmed into the central controller 45.

Each of the F, E and t parameters is taken into account through an exponential term that models saturation effects. The saturation effect takes into account the asymptotic nature of lesion formation, wherein lesion growth approaches a size limit at infinite time. Also, because the modelling of the present work is based on real data, changes in the material properties of the tissue under ablation are accounted for (e.g., changes in the electrical resistivity, which affects the quantity of the heat generated by the joule heating effect).

Figure 5:
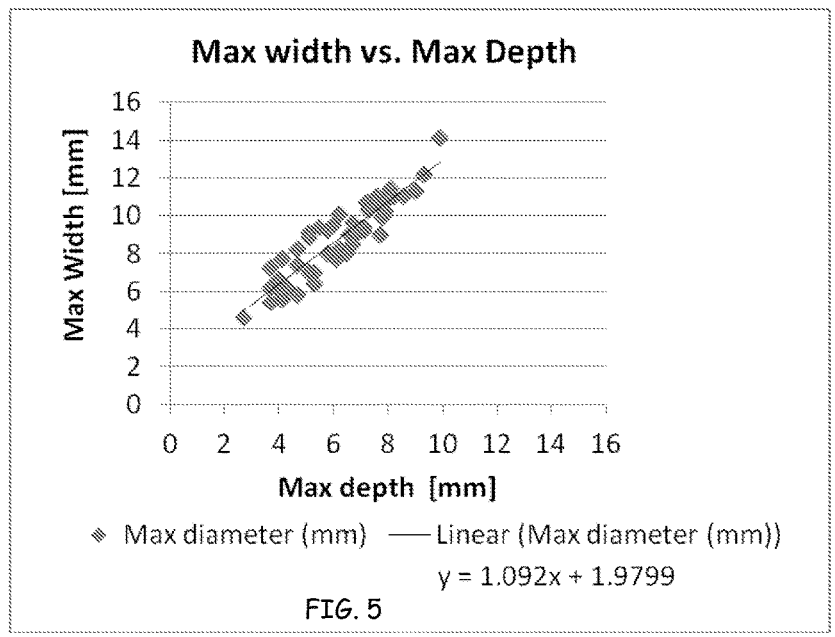
FIG. 5 is a graphical representation of the correlation between the lesion width and the lesion depth parameters used in embodiments of the invention.

Referring to FIGS. 4A-4F, data showing the exponential form of the LSI is depicted in an embodiment of the invention, demonstrating similar forms of the various lesion width and the lesion depth parameters. For these data, the energization parameter E is electrical current. Referring to FIG. 5, the correlation between the lesion width and the lesion depth parameters is observable. For the data presented in FIG. 5, a correlation of R=0.91 is realized. The high correlation confirms that the same model can be applied to calculate both the lesion depth index (LDI) and the lesion width index (LWI).

The retrospective equation that describes the LSI model can be of the following general form $$LSI(F, I, t) = k_1 * (f_2(1 - e^{-F/f_1}) + f_0) * \qquad \text{Eq. (9)}$$
$$i_2(1 - e^{-(I/i_1)^2}) * \left((1 - k_0) + k_0 \frac{1 - e^{-t/\tau}}{1 - e^{-T/\tau}}\right)$$

where $f_0$, $f_1$, and $f_2$ are force parameter coefficients, $i_1$ and $i_2$ are electrical current coefficients, $k_0$ is a diffusive heating coefficient, $k_1$ is a rescaling coefficient and $\tau$ is a characteristic time value. The input units for the LSI are gmf for the force F, milliamps (mA) for the current I and seconds (sec) for the duration time t. The resulting output of Eq. (9) correlates with a length that is expressed in millimeters.

The LSI model reflected in Eq. (9) comprises a joule heating component $(1-k_0)$ that is independent of time and a diffusive heating component $$k_0 \frac{1 - e^{-t/\tau}}{1 - e^{-T/\tau}}$$

that is a function of time. The joule heating and diffusive heating components are multiplied by the lesion depth estimated for an ablation lasting a time period of T, with the averaged force F and electrical current I over the time period T. Data analyzed for this work was generated for a time period T of 60 seconds. It is noted that the baseline time of 60 seconds was a result of the availability of lesion data that was based on 60 second ablation times. Data from ablations of different durations (e.g., 30 sec., 45 sec.) can also be utilized in a form similar to Eq. (9) by substitution of the appropriate time for the "60" found in the numerator of the diffusive heating component.

The retrospective equation of Eq. (9) is a separable variable function of contact force F, electrical current I and duration time t of the ablation. The parameters of this equation were obtained by best fit of experimental data acquired during preclinical studies. The same general form was utilized to calculate both the LDI and the LWI. Only the best fit coefficients differ between the equations. The various coefficients are presented in Table 1:

TABLE 1

Best fit coefficients for LDI and LWI equations

| | f2 | f1 | f0 | i2 | i1 | k0 | k1 | r |
|---|---|---|---|---|---|---|---|---|
| Lesion Depth Index | 4.36 | 20.67 | 2.17 | 2.57 | 630.75 | 0.578 | 1.22/√2 | 38.57 |
| Lesion Width Index | 3.74 | 18.20 | 1.99 | 3.29 | 525.85 | 0.481 | 1.10 | 29.23 |

The $k_0$ for the LDI includes a separate $\sqrt{2}$ factor in the denominator for conversion from maximum depth to effective depth. That is, if the LDI of the effective depth is desired, the $\sqrt{2}$ factor should be included in the calculation.

By implementation of Eq. (9), the central controller 45 can apprise operators of the estimated lesion growth in essentially real time, as the ablation is in progress.

Development of the lesion width index (LWI) is now described. The LWI model considers two aspects of lesion development when computing the lesion width in real time: the completed portion of the growth of the lesion width and the uncompleted portion of the growth of the lesion width, based on a total time T. As explained above, the total time T for this work is 60 seconds because that was the total time of the ablations for the data analyzed for the modelling. Based on observations of the data and the exponential behaviour attributed to saturation, the LWI uses the exponential functions of time. The exponential function can be function of previous time step exponential plus an increment:

$$f(t_1)=A(1-e^{-t1/\tau})=f(t_0)+(A-f(t_0))(1-e^{-\Delta t/\tau}), \Delta t=t_1-t_0 \qquad \text{Eq. (10)}$$

Calculations can be gated to be performed only at the time step $\Delta t$ (1 second, for example) in the interest of computational economy.

In one embodiment, calculations are made with force and current averaged over a migrating averaging window, i.e. over the last n seconds. The migrating averaging window helps account for the phenomena of thermal latency, as explained in S. K. S. Huang and M. A. Wood, Catheter Ablation of Cardiac Arrhythmia, Elsevier, 2006, chapter 1, which is hereby incorporated by reference in its entirety except for express definitions contained therein. Thermal latency is the mechanism by which the temperature and growth of the lesion continue to rise that after energization ceases. Huang and Wood, for example, report that the temperature of the lesion continues to rise for an additional 6 seconds after cessation of energization. Accordingly, in one embodiment, the time period for the migrating averaging window is 6 seconds.

In part because of the thermal latency effect, the evolution of the lesion is not well known for the first 6 seconds of ablation. Lesions are analyzed post-ablation, and the size of the lesions for short duration ablations is dwarfed by the thermal latency effect. Accordingly, in one embodiment, the LWI is calculated within the first 6 seconds of ablation as a linear interpolation between the origin and the value expected at 6 seconds.

The estimation of what the lesion width would be at time $t=T$ of ablation ($LWI_T$) is the width that the lesion would reach if constant current and force were applied during the whole time period T:

$$LWI_T(F,I)=LWI(F,I,t=T)=k_1*(f_2(1-e^{-F/f_1})+f_0)*i_2$$
$$(1-e^{-(I/i_1)^2}) \qquad \text{Eq. (11)}$$

The joule heating component of the lesion width index ($LWI_{JH}$) accounts for the tissue that is heated directly by passage of electrical current applied by the catheter. In one embodiment, $LWI_{JH}$ is thus assumed as the source of heat which then diffuses in the tissue. The $LWI_{JH}$ can also be defined as a constant ratio of the LWI at the total time T (i.e., $LWI_T$):

$$LWI_{JH}=LWI_T \qquad \text{Eq. (12)}$$

That is, in one embodiment, the $LWI_{JH}$ component of the lesion formation is constant with respect to time, but is still variable with respect to the energization parameter E and the applied contact force F.

The complete portion of the growth of the lesion width is taken as the LWI at the last time step t0 ($LWI_{t0}$), or the lesion size due to new joule heating $LWI_{JH}$ if it exceeds the lesion at $LWI_{t0}$.

$$\max\{LWI_{t0}, LWI_{JH}\} \qquad \text{Eq. (13)}$$

The uncompleted portion of the growth of the lesion is driven by the $LWI_T$ and the $LWI_{JH}$ (both using average force and current on the previous 6 seconds).

The actual LWI at time $t_1$ ($LWI_{t1}$) is the $LWI_{t0}$ plus an incremental lesion $\Delta LWI$.

$$\Delta LWI = \left(\frac{LWI_T * k_0}{k_3} - [\max\{LWI_{t0}, LWI_{JH}\} - LWI_{JH}]\right)(1 - e^{-\Delta t/\tau}) \quad \text{Eq. (14)}$$

$$\Delta t = t_1 - t_0,$$
$$k_3 = 1 - e^{-T/\tau}$$

$$LWI_{t1} = \max\{LWI_{t0}, LWI_{JH}\} + \Delta LWI \quad \text{Eq. (15)}$$

Subtracting the $LWI_{JH}$ from the completed portion of the growth of the lesion demonstrates that the exponential characteristics of the LWI and the $\Delta LWI$ only applies on the diffusive component.

It is noted that the development of the lesion depth index (LDI) is the same as the development of the LWI because both indexes have the same form and are driven by the same physics. Accordingly, the derivation of LDI is the same as for the LWI, albeit using different data (i.e., depth data).

The lesion volume can be inferred from the lesion width by multiplying a cubic of the maximum width of the lesion by a constant. In one embodiment, the equation is for converting from maximum lesion width to lesion volume is given by $$\text{Lesion volume} = 0.125167 * \pi * [\text{MAX WIDTH}]^3 \quad \text{Eq. (16)}$$

Based on data analyzed for this work, Eq. (16) has a correlation coefficient of R=0.99. Because LWI is based on the maximum width of a lesion, the LVI is related to the LWI in the same way:

$$\text{Lesion Volume Index} = 0.125167 * \pi * LWI^3 \quad \text{Eq. (17)}$$

Figure 6A:
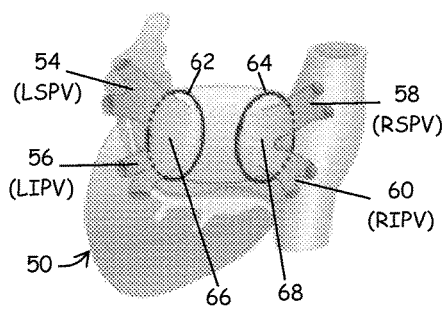
FIGS. 6A through 6D are perspective views of a human heart, showing typical preferred locations of isolation lines for various embodiments of the invention.
Figure 6B:
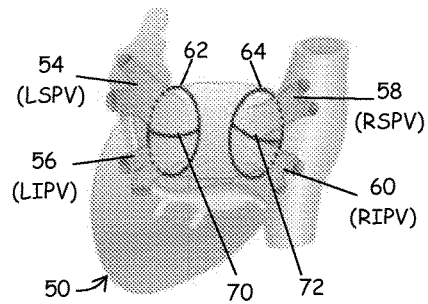
Figure 6C:
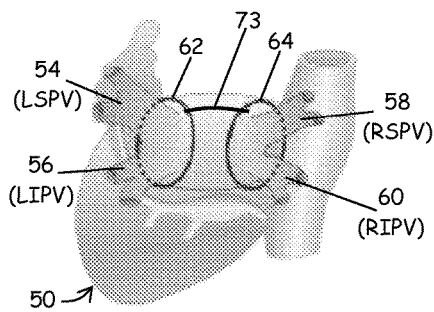
Figure 6D:
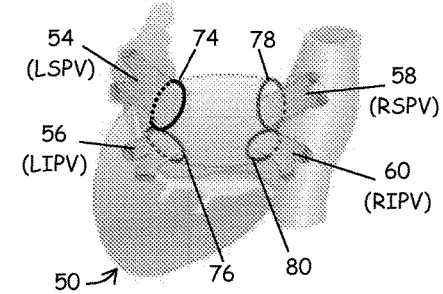

Referring to FIGS. 6A-6D, depictions of perspective views of the human heart 50 are presented, showing typical preferred locations of isolation lines for various embodiments of the invention. The depictions present the left atrium in the forefront, including the left superior pulmonary vein (LSPV) 54, the left inferior pulmonary vein (LIPV) 56, the right superior pulmonary vein (RSPV) 58 and the right inferior pulmonary vein (RIPV) 60. In FIG. 6A, desired isolation lines 62 and 64 encircle the left pulmonary veins (LSPV 54, LIPV 56) and the right pulmonary veins (RSPV 58, RIPV 60), respectively. Carinas 66 and 68 are located between the left superior and inferior veins 54, 56 and the right superior and inferior veins 58, 60, respectively. In FIG. 6B, additional desired isolation lines 70 and 72 traverse the respective interiors of the desired isolation lines 62 and 64, each substantially along the respective carina 66, 68. In FIG. 6C, an additional isolation line 73 is defined that connects the desired isolation lines 62 and 64 line along the roof of the left atrium. In FIG. 6D, desired isolation lines 74, 76, 78 and 80 surround the base of each pulmonary vein separately, i.e., LSPV 54, LIPV 56, RSPV 58 and RIPV 60, respectively. While the depictions represent full ablation lines, partial ablation lines (i.e., ablation lines that do not form a closed loop) can also be utilized.

Referring to FIG. 7A, a schematic of the left atrium with left veins 84 and right veins 86 is presented, along with the desired isolation lines 62 and 64, for use in a "zoned" accounting method in an embodiment of the invention. In the zoned accounting method, the desired isolation lines 62 and 64 can be divided into ablation zones. In one embodiment, the desired isolation lines 62 and 64 are divided into eight ablation zones each (ablation zones I-VIII and ablation zones IX-XVI). This corresponds to approximately two or three lesions per zone for nominal lesion sizes on the order of 6 to 10 mm diameter each. A plurality of lesions 87a through 87h (referred to collectively as lesions 87) are also schematically depicted in FIG. 7A, each denoted by a "circle-x" symbol (⊗). The lesions 87 depict the start of an isolation line. A trace line 90 depicts the order in which the lesions 87 were formed, starting at lesion 87a and stepping through lesion 87h.

Lesions 87a, 87b and 87c were formed consecutively in both time and space, with each successive lesion overlapping the lesion formed immediately prior. Accordingly, no ablation zones were passed over in the creation of lesions 87a, 87b and 87c. However, lesion pair 87c and 87d, while created consecutively in time, are not adjacent in space. Instead, between the creation of lesion 87c and lesion 87d, two ablation zones were passed over, as denoted in FIG. 7A as segment 90a of trace line 90. Lesion 87c, being located in ablation zone II, and lesion 87d, being located in ablation zone V, means that ablation zones III and IV were passed over between their respective formations. In one embodiment of the invention, there is said to be a "jump" between lesions 87c and 87d because entire zones were passed over. According to one embodiment of the invention, the jump index JI is incremented by the number of ablation zones passed over in a jump. By this convention, because jump 90a passes over two ablation zones, the jump index JI is incremented by two.

Lesions 87d and 87e are a pair of consecutively formed lesions that, like lesions 87a, 87b and 87c, were formed consecutively and overlap adjacently. Therefore, no incrementing of the jump index JI is incurred between lesions 87d and 87e.

Between lesions 87e and 87f, ablation sites are passed over. However, lesions 87e and 87f are formed in adjacent ablation zones (ablation zones V and VI). Therefore, there is no "jump" and thus no incrementing of the jump index due to the sequence of lesions 87e and 87f.

In the depiction of FIG. 7A, a plurality of lesions 92 are depicted as formed along the desired ablation line 64 about the right veins 86 and in a sequence depicted by a trace line 94. Here, however, all of the lesions are formed consecutively in both time and space, with each successive lesion overlapping the lesion formed immediately prior. If this pattern were to continue all the way around the desired ablation line 64 until the isolation line fully surrounds the RSPV 58 and the RIPV 60, no incrementing of the jump index JI would occur, and the jump index JI would equal zero.

Referring to FIG. 7B, the left veins 84 are depicted, again in the zoned accounting method, with the desired isolation line 62 having been fully formed with a plurality of lesions 96, as well as the additional desired isolation line 70 having been formed along the carina 66 with a plurality of lesions 98. In FIG. 7B, a sequence line 100 depicts the order in which the lesions 96 were formed, starting with lesion 96a. Likewise, a sequence line 102 depicts the order in which the lesions 98 were formed, starting with lesion 98a. Assuming that the lesions 96 were formed first, it would be necessary to jump to the middle of zone III to begin the lesions 98. However, because all of the ablation zones received at least one ablation during the formation of the lesions 96, incrementing of the jump index JI is terminated. Therefore, the jump index would not be incremented as a result of the treatment of the carina in this instance. If, however, the carina were treated prior to the formation of at least one lesion in all the zones, movement of the ablation head to the carina from a non-adjacent zone (i.e., from zones other than zones III or VII) would cause the jump index JI to be incremented.

Referring to FIG. 7C, the right veins 86 are depicted in a zoned accounting method with the desired ablation lines 78 and 80 of FIG. 6D in an embodiment of the invention. A plurality of lesions 104 are depicted as being formed in contact with the desired ablation line 78. A trace line 106 depicts the order in which the lesions 104 are formed, starting with lesion 104a, with the remaining lesions 104 being formed consecutively to overlap with the lesion formed immediately prior thereto. In one embodiment, treatment of the carina before completion of all the zones of the isolation line is treated as a "jump," and the jump index is therefore incremented by 1 in forming the lesions 104, even though the lesions 104 of FIG. 7C are depicted as being formed consecutively and in an overlapping manner.

A plurality of lesions 108 are depicted as being formed in contact with the desired ablation line 80. A trace line 110 depicts the order in which the lesions 108 are formed, starting with lesion 108a, with the remaining of the plurality of lesions 108 being formed consecutively to overlap with the lesion formed immediately prior thereto. Assuming the lesions 104 are formed first and in the order depicted in FIG. 7C, one would have to reposition the ablation catheter from zone IX to zone XI in order to form the first lesion 108a in the line. The attendant jump would pass over zone X. Because some of the ablation zones remain untreated (i.e., zones XII, XIII and XIV), incrementing of the jump index JI is still active and the passing over of zone X would thus causing the jump index JI to be incremented by 1.

Any number of ablation zones can be utilized for defining the resolution of the jump index JI. For example, the number of zones could be doubled, thus providing a jump index JI having a higher resolution. Or the number of ablation zones could be reduced to provide a jump index having a coarser resolution. Furthermore, the ablation zones do not have to be of equal tangential dimension. For example, ablation zones II, III and IV could be combined into one ablation zone. This provides greater resolution for the jump index JI about the smaller ablation zones. In this way, the jump index can be tailored for greater sensitivity in regions more prone to gap formation.

In various embodiments of the invention, the jump index JI can be used in combination with either the minimum force-time integral FTI or the minimum lesion size index LSI utilized in the formation of the isolation line for predicting the post-operative formation of gaps. Empirical relationships have been developed to quantify this effect, using a total of 3164 ablations performed in the formation of a total of 99 PV lines over a total of 50 patients, and using eight zones per pair of ipsilateral veins as depicted in FIGS. 7A and 7B. The data is presented in Tables 2 and 3 below for JI vs. minimum FTI and JI vs. minimum LSI, respectively. The data from Tables 2 and 3 are also presented in FIGS. 8A and 8B, respectively. The specific form of the FTI used for the data of Table 2 is the force over time (FOT) form of Eq. (1) above.

TABLE 2

Gap formation rate as a function of FTI and JI

| | Jump Index | | |
|---|---|---|---|
| FTI | ≤5 | 6 ≤ JI ≤ 11 | ≥12 |
| >400 | 1% | 5% | 20% |
| 200-400 | 2% | 17% | 15% |
| <200 | 7% | 14% | 30% |

TABLE 3

Gap formation rate as a function of LWI and JI

| | Jump Index | | |
|---|---|---|---|
| LWI | ≤5 | 6 ≤ JI ≤ 11 | ≥12 |
| >6 | 0% | 6% | 20% |
| 4-6 | 2% | 10% | 22% |
| <4 | 7% | 14% | 22% |

Both sets of data show the same trends. Specifically, the chance of gap formation increases generally with jump index JI and decreases generally for increasing minimum LWI values and for increasing minimum FTI values. The minimum LWI and JI data of Table 3/FIG. 8B indicate an increase in the chance of gap formation that is substantially monotonic with both increasing jump index and decreasing minimum LWI.

Figure 8A:
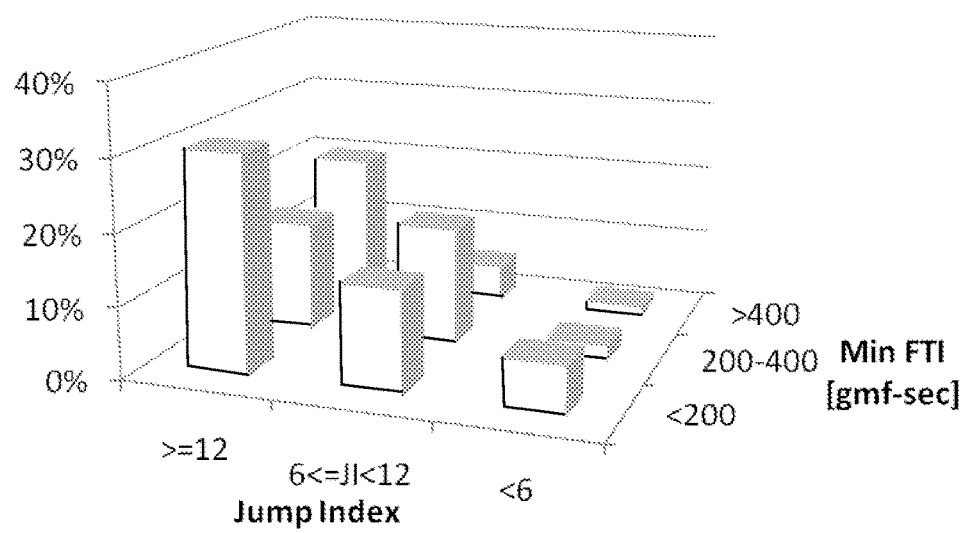
FIGS. 8A and 8B depict gap formation rates for a zone-based jump index (JI) vs. minimum force-time integral (FTI) and for jump index (JI) vs. minimum lesion width index (LWI), respectively, in embodiments of the invention.
Figure 8B:
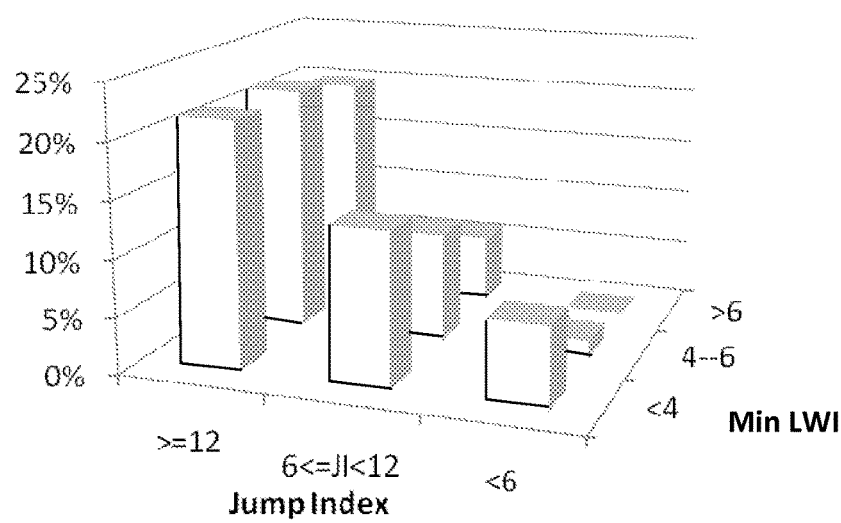

The data of Tables 2 and 3/FIGS. 8A and 8B support the conclusion that formation of lesions sequentially in both time and space is advantageous. Furthermore, the tables provide a way to predict the likelihood of gap formation based on the jump index JI, minimum FTI and/or minimum LWI. For example, if, during the course of forming an isolation line a jump index JI of 7 was accrued and a minimum lesion width index LWI of 8 was observed, there would be a 6% chance that a gap would develop along the isolation line. In terms of minimum FTI, the same JI=7 in conjunction with a minimum FTI of 350 gmf-sec during the ablation line formation would equate to a 17% chance of gap formation.

Figure 9A:
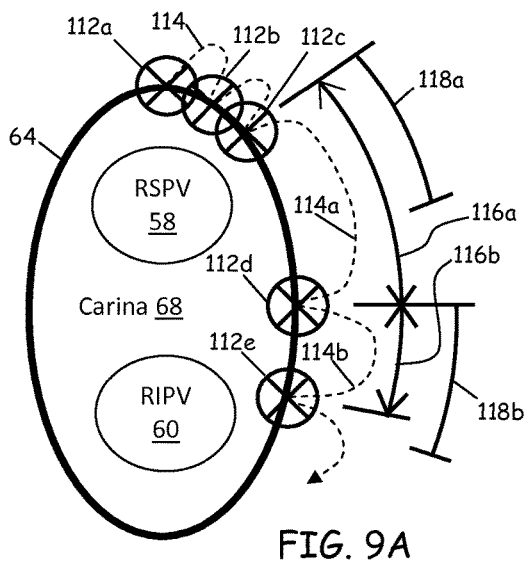
FIGS. 9A and 9B depict a distance-based method for tracking the jump index in an embodiment of the invention, distinguishing it from zone accounting methods.
Figure 9B:
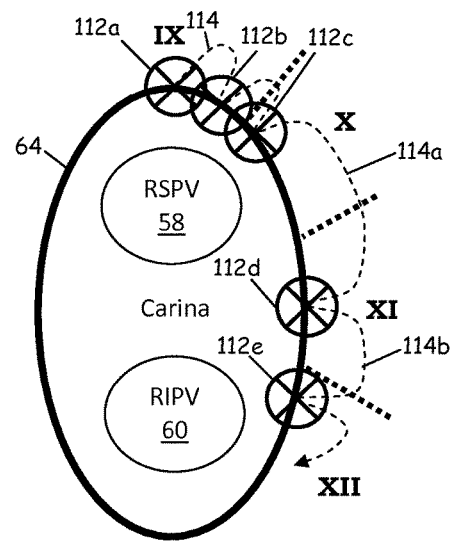

Referring to FIGS. 9A and 9B, a distance-based accounting technique for computing the jump index JI is depicted in an embodiment of the invention, and distinguished from the zoned accounting method. The right veins 58, 60 are again depicted with the desired ablation line 64 of FIG. 6A. A plurality of lesions 112a through 112e are depicted as having been formed along the desired ablation line 64 and in a sequence depicted by a trace line 114. Trace segments 114a and 114b, depicted between lesions 112c/112d and 112d/112e, respectively, depict that lesions 112c, 112d and 112e were formed sequentially but not with continuity. Measured arc lengths 116, depicted individually as 116a and 116b, represent the distances between the centers of lesions 112c/112d and 112d/112e, respectively, along the desired ablation line 64. Reference arc lengths 118, depicted individually as 118a and 118b, are also depicted adjacent the measured arc lengths 116a and 116b, respectively.

With distance-based accounting of the jump index JI, a "jump" occurs when the arc distance between consecutively formed lesions along a desired isolation line exceeds a predetermined distance. In the depiction of FIG. 9A, the reference arc length 118 represents predetermined lengths upon which incrementing of the jump index JI is based. If the measured arc length 116 between consecutive lesions exceeds the respective reference arc length 118, the jump index JI is incremented. If the measured arc length 116 between consecutive lesions does not exceed the respective reference arc length 118, the jump index JI is not incremented. By this methodology, the trace segment 114a represents a jump that causes the jump index JI to be incremented because measured arc length 116a is greater than reference arc length 118a. In contrast, the trace segment 114b does not represent a jump that would cause the jump index JI to be incremented because measured arc length 116b is less than reference arc length 118b. The reference arc lengths 118a and 118b can be of varying length dependent on location on the desired ablation line 64, or they can be of the same length.

In one embodiment, the jump index JI can incur multiple increments from a single jump according to a ratio of the measured arc length 116 to the respective reference arc length 118. For example, if arc length 116a is 1.6 times longer than reference arc length 118a, the jump index could be simply the ratio (i.e., 1.6), or rounded down to the base integer (i.e., 1) or rounded to the nearest integer (i.e., 2). Other incrementing schemes can be developed based on the length of the measured arc lengths 116, location relative to the pulmonary veins, or other observations garnered from lesion formation data.

In one embodiment of distanced-based accounting, the jump index JI is incremented until the maximum arc length between any two lesions along the desired isolation line is less than the predetermined arc length. In another embodiment, a hybrid between the zone-based and the distance-based accounting techniques can be implemented. For example, jumps can be detected in accordance with distance-based accounting until at least one lesion is formed in all of the zones of a zone-based segmentation.

In FIG. 9B, the same lesions 112a-112e and trace line 114 is overlaid on the zone-segmented scheme of FIG. 7A to contrast the distance-based accounting technique with the zoned accounting technique. The reference arc lengths 118a and 118b represent the same length as one of the zones X and XI of FIG. 9B. Yet the zoned accounting method would not result in an incrementing of the jump index JI because none of the zones are entirely passed over between lesions.

Figure 10:
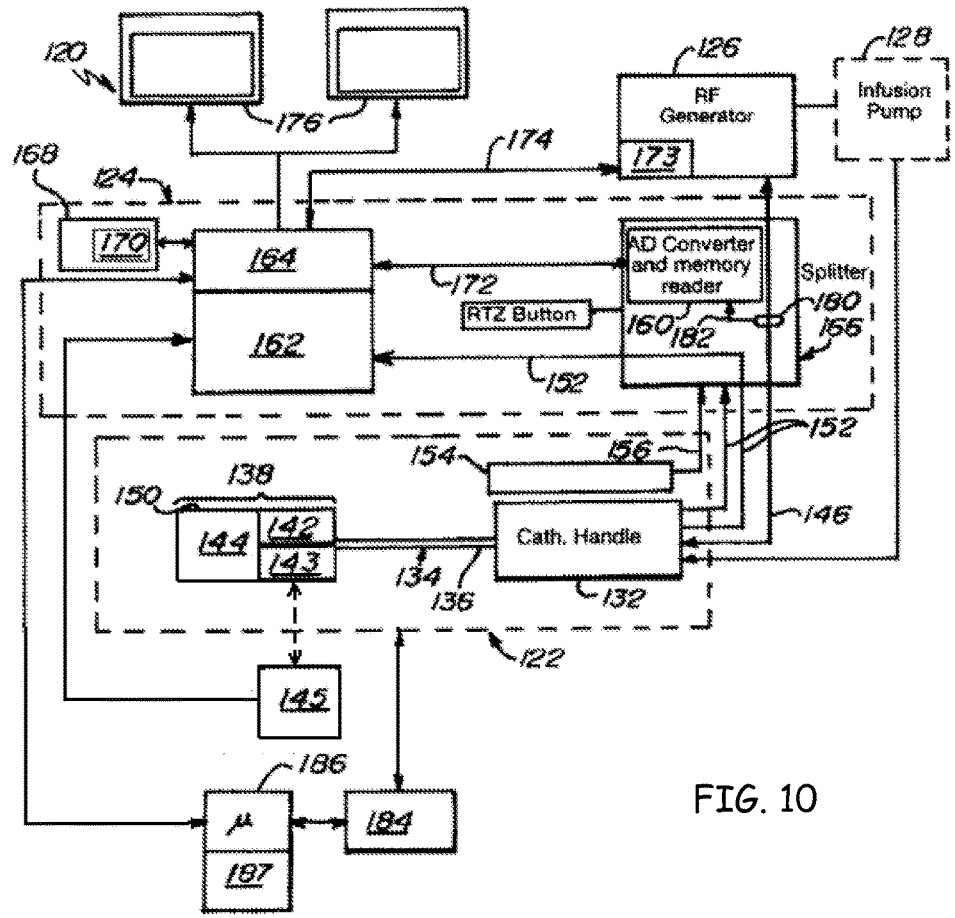
FIG. 10 depicts a schematic of a contact ablation system in an embodiment of the invention.

Referring to FIG. 10, a force sensing catheter-based point contact ablation system 120 is depicted in an embodiment of the invention. The system 120 comprises a force sensing catheter assembly 122 operatively coupled to a data acquisition and processing unit or control system 124, a power source 126 and an infusion pump 128. The catheter assembly 122 may include a handle portion 132 operatively coupled with an elongate, flexible catheter 134 having a proximal portion 136 and a distal portion 138. The catheter assembly 122 may also include a digital memory device 154 for storage of calibration parameters specific to the force sensor 142 and coupled to the control system 124 via a computer cable 156.

The distal portion 138 includes a contact ablation probe or ablation head 144 operatively coupled with a force sensor 142 and a position sensor/emitter 143. The ablation head 144 may comprise one or more electrodes operatively coupled to the power source 126 via a power cable 146. The ablation head 144 may also include one or more temperature sensors 150. The force sensor 142 is adapted to output a signal in response to a contact force exerted on the ablation head 144. Signals from the force sensor 142 and temperature sensor 150 (when present) may be routed to the control system 124 via instrumentation cabling 152.

The position sensor/emitter 143 represents various forms of three-dimensional position sensing available in the art. Examples of such sensing and/or emitting devices that are operatively coupled to the ablation head 144 includes: electromagnetic mapping, such as the Aurora system marketed and sold by NDI of Waterloo, Ontario, Canada; electric mapping, such as the EnSite Velocity system marketed by St. Jude Medical of St. Paul, Minn., U.S.A.; fluoroscopic imaging; ultrasound echo techniques; magnetic resonance imaging (Mill) techniques; fiber optic shape and position sensing. Such systems are known in art and provide the capability of locating the position of the ablation head in three-dimensional space. Certain positioning systems (e.g., fiber optic shape and position systems) can provide three-dimensional position information from the position sensor 143 to the control system 124 via the instrumentation cabling 152 (see, e.g., U.S. patent application Ser. No. 12/127,657, filed 27 May 27, 2008, now U.S. Pat. No. 8,622,935, issued 7 Jan. 2014, assigned to the assignee of the instant application, and hereby incorporated by reference herein in its entirety except for express definitions contained therein). Other systems (e.g., MRI and fluoroscopic imaging) may require a receiver 145 operatively coupled to receive signals actively emanating from the position emitter 143, or a receiver 145 responding to signals passively reflected from or transmitted through or past the position emitter 143 (e.g., transesophegal echo). In such systems, the receiver 145 is configured to send information regarding the spatial position of the ablation head 144 to the control system 124.

The control system 124 may include an analog-to-digital (A/D) converter 160, a force conversion module or force signal conditioning system 162 and a controller or processor 164, all of which may be operatively coupled to an interface 166. In other embodiments, communication with the control system can be done through a communication bus such as a RS-485 bus, an Ethernet bus or a wireless connection. The interface 166 may include connection for the various cabling 146, 152, 156 from the force sensing catheter assembly 122, and may also be operatively coupled to a tare or zero reset for zeroing the force sensor 142. The processor 164 may include or have access to a storage medium 168 that contains programming instructions 170 to be carried out by the processor 164. The processor 164 may also control and log data from the force signal conditioning system 162, and may also communicate with the A/D converter 160 via a communications cable 172, such as a RS-422 cable. In one embodiment, the power source 126 is equipped with an output controller 173 operatively coupled to the processor 164 via a control line 174 for computer control of the power output. One or more displays 176 can act as a receiving device(s) that receives instructions and other real time information from the processor 164, for example for conveying the information to an operator controlling the flexible catheter 134. A non-limiting example of the rate at which information is logged by the processor 164 is approximately 60-Hz. A non-limiting example of the rate at which the displays are updated is approximately 10-Hz.

Force sensing can be achieved with strain sensors or distance/displacement sensors that sense the movement of a deformable body. Strain sensors include common resistive strain sensors, piezoelectric and piezoresistive elements and MEMS sensors. Distance sensors include capacitive, inductive and optical sensor technologies. For example, certain distance sensors utilize a single magnetic emitter opposite three pickup coils to measure the local intensity changes at each coil and therefore the strain on the body.

Generally, the force signal conditioning system 162 comprises equipment for driving or sourcing the sensing element or elements of the force sensor 142 and/or digitizing or monitoring an output of the force sensor 142. For example, if the force sensor 142 implements foil-type strain gauges in a Wheatstone bridge configuration, the force signal conditioning system 162 may include an excitation source, a signal conditioner for conditioning and amplification of the output of the Wheatstone bridge, and an A/D converter (not depicted). The force signal conditioning system 162 may also include firmware that converts the digitized output into engineering units (e.g., newtons, pounds-force or grams-force). Alternatively, the digital signal may be converted to engineering units by the processor 164.

In one embodiment, the force sensor 142 comprises one or more fiber optic strain elements, such as fiber Bragg grating(s) or Fabry-Perot resonator(s). In this embodiment, the instrumentation cabling 152 includes fiber optic cables and the force signal conditioning system 162 comprises a fiber optic interrogator, such as the Micron Optics model is SM125 (for fiber Bragg grating interrogation) and the FISO model FCM (for Fabry-Perot interrogation).

A current detector 180 may be operatively coupled with the power cable 146 for detection of the electrical current flowing to the ablation head 144. The current detector 180 may be operatively coupled to the A/D converter 160 for processing by the processor 164. In one embodiment, the current detector 180 comprises a conductive coil surrounding the power cable 146 which produces an output signal 182 proportional to the magnetic field generated by the AC current passing through the power cable 146.

In one embodiment, a robotic manipulator 184 can be operatively coupled with the force sensing catheter assembly 122. The robotic manipulator 184 acts as a receiving device for controlling the flexible catheter 134. In one embodiment, the robotic manipulator 184 is a stand-alone device operatively coupled to a local microprocessor controller 186, which receives instructions from a user via a local interface 187, and/or from the processor 164 (FIG. 10). Alternatively, the robotic manipulator 184 can be integrated with the system 120, responding to instructions directly from the processor 164, which may eliminate the need for a separate microprocessor controller and attendant interface.

Functionally, the force sensor 142 and the current detector 180 and/or the output controller 173 can provide contact force F, energization parameter E and time duration t information that can be utilized by the processor 164 to calculate the lesion size index LSI (i.e., the LDI, LWI and/or LVI), from which lesion size information can be calculated and displayed on the display(s) 176. The three-dimensional position information provided to the control system 124 to calculate the position of the next ablation for display on the display(s) 176. The three-dimensional position information can also be utilized when tracking the jump index JI. In one embodiment, the display(s) 176 can include both output from a particular visualization system being utilized during the procedure (e.g., fluoroscopy or transesophagal echo) along with a computer-generated three-dimensional image reflecting the position and control information determined by various embodiments of the present invention. In another embodiment, a display 176 can present a combined or overlaid set of images of the visualization system output together with the positional and control information provided by various embodiments of the present invention.

The robotic manipulator 184 can be made to respond to the commands of the local microprocessor controller 186 to control the movement of the catheter 134 and the magnitude of any subsequent reaction force exerted on the ablation head 144. The movement may be the controlled parameter in a closed loop control scheme, and the force measured by the force sensor 142 the feedback measurement. A desired force set point or desired force interval set point may be provided to the local microprocessor controller 186 by an operator via the local interface 187 or via the processor 164.

Figure 11A:
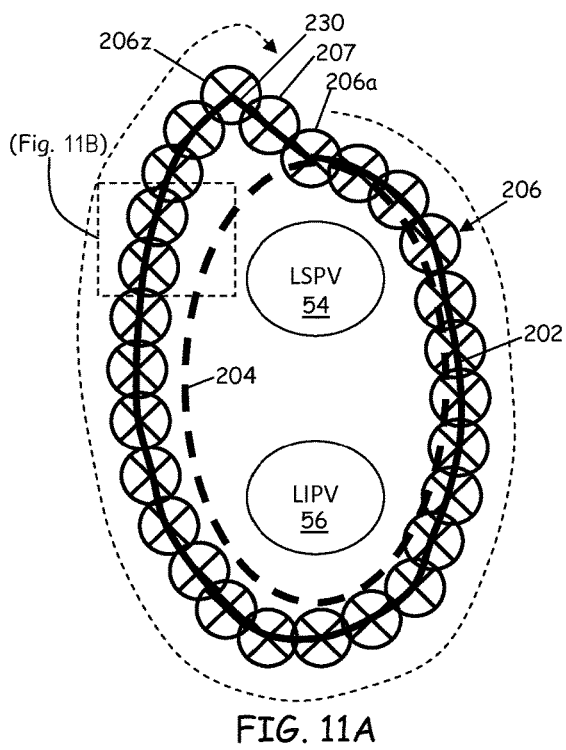
FIGS. 11A through 11C depict aspects of a variable reference line method in an embodiment of the invention.
Figure 11B:
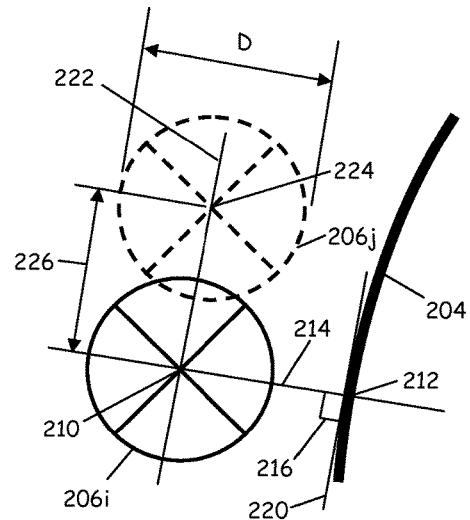

Referring to FIGS. 11A and 11B, a variable reference line method for forming an isolation line 202 is depicted and described in an embodiment of the invention. In FIG. 11A, the left pulmonary veins (LSPV 54, LIPV 56) are depicted as surrounded by a predetermined desired ablation line 204 and a plurality of lesions 206. The variable reference line method involves establishing a desired location for a first lesion 206a that is on the desired ablation line 204. However, for a variety of reasons, the actual location of the lesion 206a may not be in perfect alignment with the prescribed location or be centered on the desired ablation line 204. These reasons include the dynamic nature of the target tissue (a beating heart), operator experience, etc.

After formation of the first lesion, a desired location for each subsequent lesion of the plurality of lesions 206 can be determined by extrapolating from the actual location of a center 210 of the most recently formed lesion 206i (rather than along the desired ablation line 204), as depicted in FIG. 11B. The extrapolation can be performed by locating where the most recently formed lesion 206i is with respect to the desired ablation line 204. This can be done by determining an intersection point 212 of a line 214 that passes through the center 210 of the most recently formed lesion 206i and intersects the desired ablation line 204 at a right angle 216. A slope 220 of the desired ablation line 204 at the intersection point 212 can then be determined. A projection line 222 can then be extrapolated from the center 210 of the most recently formed lesion 206i at the same slope 220, along which a center 224 of a desired location of the next lesion 206j to be formed is located. A distance 226 between the center 210 of the most recently formed lesion 206i and the center 224 of the desired location of the next lesion 206j can be established that provides reasonable assurance that the next lesion 206j will overlap with the most recently formed lesion 206i. For example, the distance 226 can be set at some fraction f of the expected diameter D of the lesions being formed (e.g., f=0.75).

The extrapolation technique of the variable reference line method continues around the ipsilateral pulmonary veins until hopefully an isolation line is formed. Preferably, the plurality of lesions 206 remain in close proximity to the desired ablation line However, there may be instances where the actual isolation line 202 is biased in one direction (e.g., radially outward, as depicted in FIG. 11A) relative to the desired ablation line 204. In this case, the lesions 206a-206z will not form a closed isolation line, but instead forms an open isolation line, as depicted in FIG. 11A.

In FIG. 11A, it can be determined that lesion 206z would have closed the isolation line if it, along with the other lesions 206, were in closer proximity to the desired ablation line 204. That lesion 206z should have closed the line can be determined by checking whether its respective intersection point 212 with the desired ablation line 204 is within a diameter D of the first lesion 206a. At that point, if the actual location of the center of lesion 206z is more than a distance D away from the center of lesion 206a, a straight line 230 is established between lesions 206z and 206a and the desired location of a supplemental lesion 207 is established along the straight line at a distance off D from the center of lesion 206z. Lesions can prescribed along the straight line 230 until closure of the isolation line is obtained.

It is noted that, herein, "206z" does not denote a certain numbered lesion—e.g., lesion #26—but rather denotes the last lesion formed before implementation of the straight line 230. Also, lesion(s) 207 denote lesions that are formed that are targeted for the straight line 230.

Figure 11C:
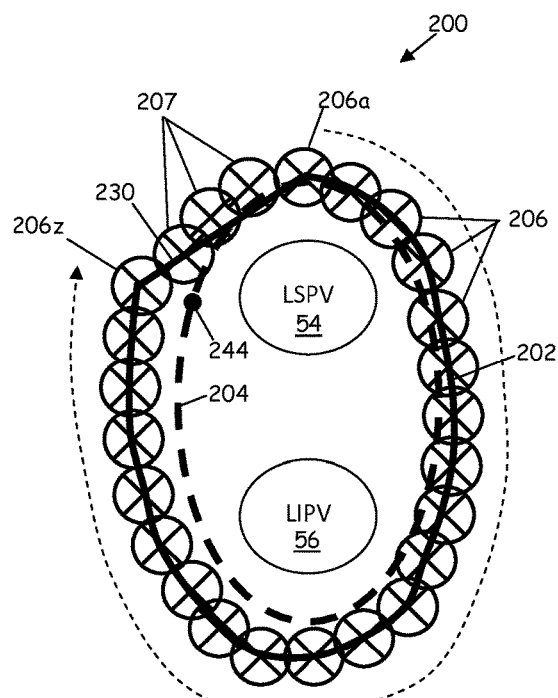

Referring to FIG. 11C, the calculation of the straight line 230 can be established before arriving at the location of expected closure of the isolation line. That is, projection of the straight line 230 and the formation of lesions thereabout can be started upon reaching or first exceeding a predetermined location 244 on the desired ablation line, thus making the transition to closure of the isolation line 202 less tortuous.

To aid the operator in performing the various lesion patterns depicted in FIG. 6 and FIG. 7, various steps of the variable reference line method described above can be included in the programming instructions 170 of the control system 124 for access by the processor 164.

Figure 12A:
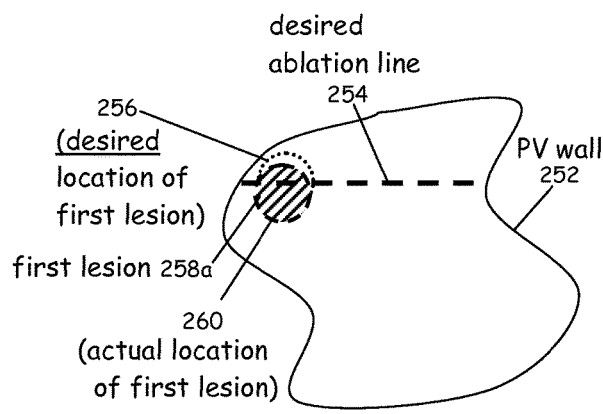
FIG. 12A through 12D depict aspects of a fixed reference line method in an embodiment of the invention.

Referring to FIGS. 12A-12D, a fixed reference line method for forming an isolation line is presented in an embodiment of the invention. In FIG. 12A, a PV wall 252 is depicted upon which a desired ablation line 254 is ascribed. A desired location 256 for a first lesion 258a is established, centered on the desired ablation line 254. An actual location 260 of the first lesion 258a is measured during the ablation. The actual location 260 may differ from the desired location 256.

Figure 12B:
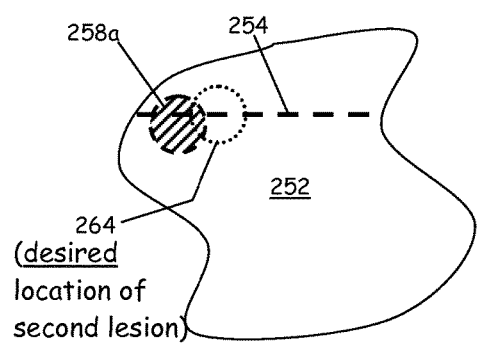

In FIG. 12B, establishment of a desired location 264 for a second lesion 258b is depicted. A desired location of a subsequent lesion can be determined by calculating where a lesion of an anticipated diameter centered on the desired ablation line 254 would overlap the previously formed lesion. In one embodiment, an estimated width or diameter of the previously formed lesion can also be inferred, for example using the lesion width index LWI of Eq. (15), and the position along the desired ablation line 254 established based on the width estimate. By this methodology, the desired location 264 is again centered on the desired ablation line 254, and centered so as to overlap with the first lesion 258a by a predetermined amount if properly placed and formed to the desired size.

Figure 12C:
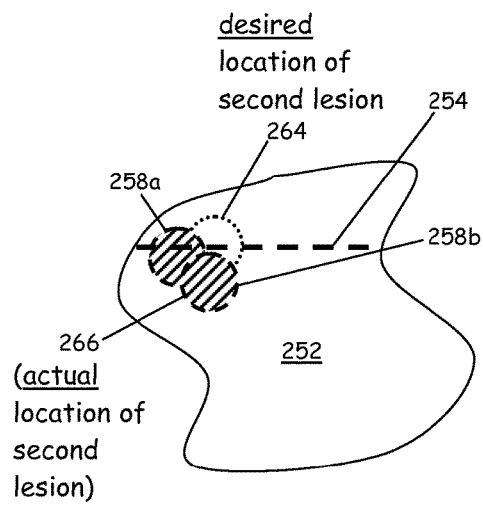
Figure 12D:
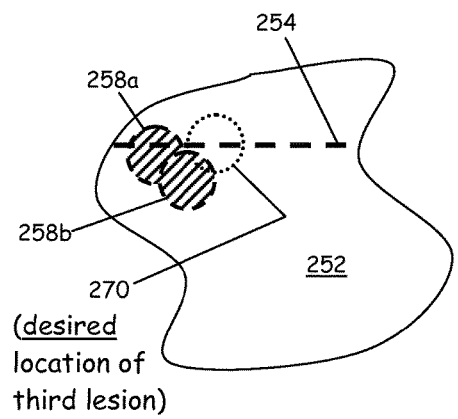

In FIGS. 12C and 12D, the second lesion 258b is depicted after formation as having an actual location 266 that is substantially out of alignment with the desired location 264. A desired location 270 of a third lesion is calculated based on the actual location 266 of the second lesion 258b.

If a lesion is formed at an actual location that is centered away from the desired ablation line 254 by a dimension that exceeds the expected diameter of ablation, there is no calculated overlap between that lesion and a subsequent lesion located on the desired ablation line 254, and the continuity of the ablation line becomes questionable. In one embodiment of the invention, the previously formed lesion can be ignored and the desired location of the previously formed lesion reestablished as the desired location of the next subsequent lesion. In other embodiments, a line between the previously formed lesion and the desired ablation line 254 can be established, and lesions formed along this line until the lesion pattern is again in contact with the desired ablation line 254.

Figure 13:
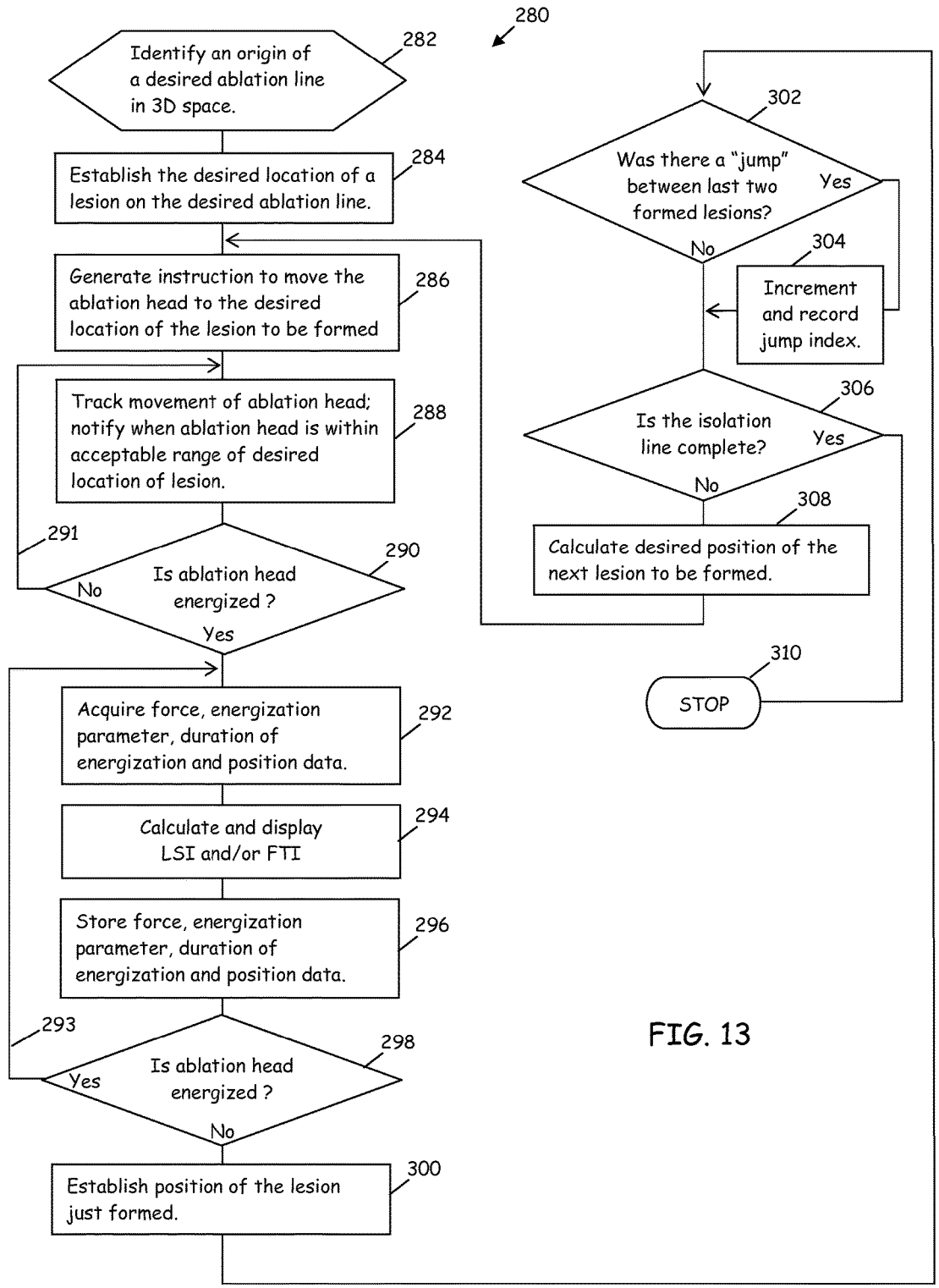
FIG. 13 is a flow chart depicting certain aspects of the variable reference line method and the fixed reference line method in embodiments of the invention.

Referring to FIG. 13, a flow chart 280 depicting certain aspects of the variable reference line method and the fixed reference line method is presented in embodiments of the invention. In certain embodiments, the actual locations of the various lesions (e.g., 260 and 266 in FIGS. 12A and 12C, respectively) are measured, for example, using the position sensor/emitter 143 of FIG. 10 to measure the location of the ablation head 144 during energization. Other parameters (e.g., contact force F, energization (e.g. electrical current I), and duration of time t) can also be measured and utilized by the central control system 124. The various steps for assisting an operator in performing the methods can also be included as programming instructions 170 for access by the processor 164.

Initially, an origin of the desired isolation line to be formed (e.g., line 62, 64, 70, 72, 73, 74, 76, 78 and 80 of FIGS. 6A through 6D) is identified in three-dimensional space (step 282). In one embodiment, the physician utilizes the visualization system to identify a present location of the ablation head 144 relative to the anatomy of the pulmonary vein (PV) or any other reference point on the heart of the patient and then correlates that location with a corresponding location in a suitable three-dimensional model. The three-dimensional model can be utilized by the processor 164 to determine the positional and control information for creating the desired isolation line. In one embodiment, the three-dimensional model is a generic model of a pulmonary vein that is maintained by the processor 164 and memory 170. In another embodiment, the three-dimensional model is an anatomical reconstruction of the pulmonary vein of the particular patient that may be loaded into the processor 164 and memory 170. In a further embodiment, a four-dimensional animated version of the anatomical model may be utilized to reflect positional movement of the PV in response to heart beats. Optionally, the patient's ECG may be used as an input for such a four-dimensional model to correlate the expected motion of the PV in response to the heart beat of the patient.

The desired location of a first lesion (e.g., the desired location of lesion 206a of FIG. 11A or desired location 256 of FIG. 12A), located on the respective desired isolation line, is identified at step 284 in accordance with any of the various embodiments previously described. The processor 164 then instructs the operator/robotic manipulator 184 to move the distal portion 138 of the flexible catheter 134 to position the ablation head 144 at the desired location (step 286).

During the positioning of the ablation head 144, the position of the ablation head 144 can be tracked by actively utilizing the position sensor/emitter 143 (step 288). The movement of the position sensor/emitter 143 (and therefore the position of the ablation head 144) can be tracked by the processor 164 and updated to the display(s) 176 by the processor 164.

The instruction to the operator/robotic manipulator 184 as well as the notifications and updates regarding movement or positioning of the ablation head 144, can be presented on the display 176 by the processor 164, for example, notifying the operator/robotic manipulator 184 that the ablation head 144 is within an acceptable range or tolerance of the desired location for the lesion to be formed (step 288). Various visual presentations can be utilized to convey the existing and desired locations of lesions along the isolation line that display different information in different colors and/or overlays of information. The instruction and notification can also be performed audibly, such as by a voice instruction or a beeping sound.

During the tracking of the movement of the ablation head, the processor 164 can also continuously monitor whether energization of the ablation head 144 has been initiated (steps 288 and 290 within loop 291). Upon energization, the processor 164 can go into a data acquisition and display mode, represented by loop 293. In the data acquisition and display mode, the force F, energization parameter E, duration time t of energization acquired (step 292) and used in the calculation and display of the lesion size index LSI and/or force-time integral FTI (step 294). The processor 164 can also store the acquired information (e.g., F, E, t and position) to electronic memory (step 296), such as (but not limited to) storage medium 168. In one embodiment, the processor 164 remains in the data acquisition and display mode 293 until energization of the ablation head ceases (step 298).

The data acquisition and display mode 293 is thus exited after the lesion is formed. In one embodiment, the position of the so-formed lesion can be determined (step 300), for example, by averaging the position data acquired during the duration of the lesion formation. In one embodiment, a determination is made whether there was a "jump" between the last two consecutively formed lesions (step 302). The step 302 can implement, for example, the zoned accounting methods or the distance-based accounting methods described above for tracking the jump index JI. In the event that a jump occurred, the processor 164 can increment the jump index and record it to the storage medium 168.

The processor 164 can also determine whether the isolation line is complete (step 306), for example by implementation of the variable or the fixed reference line methods outlined above. If it is determined that the isolation line is not complete, the desired position of the next lesion to be form can be determined (step 308). This determination can also be in accordance with the methodology described in the variable or the fixed reference line methods outlined above.

Upon completion of the prescribed ablation lines, the automatic generation of control information can be ceased (step 310).

Each of the features and methods disclosed herein may be used separately, or in conjunction with other features and methods, to provide improved devices, systems and methods for making and using the same. Therefore, combinations of features and methods disclosed herein may not be necessary to practice the invention in its broadest sense and are instead disclosed merely to particularly describe representative embodiments of the invention.

For purposes of interpreting the claims for the present invention, it is expressly intended that the provisions of Section 112, sixth paragraph of 35 U.S.C. are not to be invoked unless the specific terms "means for" or "steps for" are recited in the subject claim.

What is claimed is:

1. A control system for determining the continuity of an isolation line formed by point contact ablation in a region of the human heart, the control system configured to be operatively coupled with an energy source, the control system comprising:
    a central controller configured to:
        store a desired isolation line;
        divide the desired isolation line into a plurality of contiguous ablation zones along the desired isolation line;
        execute the following forming and counting steps:
            forming a first lesion of a lesion pair using energy flow from the energy source, wherein the first lesion is formed in a first zone of the plurality of contiguous ablation zones;
            forming a second lesion of the lesion pair using energy flow from the energy source, wherein the second lesion is formed in a second zone of the plurality of contiguous ablation zones, wherein the second lesion is the next sequential lesion formed after the first lesion, and wherein the second zone is not adjacent to the first zone;
            counting a number of passed-over ablation zones between the lesions in the lesion pair; and
            incrementing a cumulative sum of passed-over ablation zones by the number; and
        report out an indication of the continuity of the isolation line based at least in part on the cumulative sum of passed-over ablation zones.

2. The control system of claim 1, wherein the lesion pair is a first lesion pair of a plurality of lesion pairs, and wherein the control system is further configured to repeat the forming and counting steps until at least one lesion has been formed in each zone of the plurality of contiguous ablation zones.

3. The control system of claim 1, wherein the central controller is further configured, during the dividing step, to divide the desired isolation line into eight or fewer ablation zones.

4. The control system of claim 1, wherein the central controller is further configured, during the dividing step, to divide the desired isolation line into more than eight ablation zones.

5. The control system of claim 1, wherein the central controller is further configured, during the dividing step, to divide the desired isolation line into zones of equal tangential dimension.

6. The control system of claim 1, wherein the desired isolation line encircles a pair of ipsilateral pulmonary veins.

7. The control system of claim 1, wherein the desired isolation line comprises a first isolation line and a second isolation line, wherein the first isolation line encircles a pair of ipsilateral pulmonary veins, wherein the second isolation line extends along a carina between the pair of ipsilateral pulmonary veins, and wherein the second isolation line connects between two locations along the first isolation line.

8. The control system of claim 7, wherein the central controller is further configured, during the dividing step, to divide the first isolation line of the desired isolation line into the plurality of contiguous ablation zones.

9. The control system of claim 1, wherein the desired isolation line comprises a first isolation line and a second isolation line, wherein the first isolation line encircles a first pulmonary vein of a pair of ipsilateral pulmonary veins, and wherein the second isolation line encircles a second pulmonary vein of the pair of ipsilateral pulmonary veins.

10. The control system of claim 9, wherein the first isolation line and the second isolation line are adjacent and tangentially meet along at least a portion of a carina between the first and second pulmonary veins.

11. The control system of claim 10, wherein the central controller is further configured, during the dividing step, to divide an outer perimeter of the adjacent first and second isolation lines into the plurality of contiguous ablation zones.

12. The control system of claim 1 further comprising a force sensor communicatively coupled with the central controller, and wherein the energy flow is time variant based at least in part on a contact force signal from the force sensor.

13. The control system of claim 1 further including a position sensor communicatively coupled with the central controller, wherein the central controller is further configured to:
    track an ablation head of an ablation catheter to a first position relative to the desired isolation line using position information from the position sensor;

form the first lesion of the lesion pair at the first position;

track the ablation head of the ablation catheter to a second position relative to the desired isolation line using updated position information from the position sensor; and form the second lesion of the lesion pair at the second position.

14. The control system of claim 13, wherein the central controller is communicatively coupled with a force sensor, wherein the central controller is further configured to predict ablation effectiveness using an indicator of lesion transmurality, and the indicator of lesion transmurality comprises a force-time integral based at least in part on a contact force signal from the force sensor.

15. The control system of claim 1, wherein the central controller is further configured, during the forming and counting steps, to:

form a third lesion of a second lesion pair using energy flow from the energy source, wherein the third lesion is formed in a third zone of the plurality of contiguous ablation zones;

form a fourth lesion of the second lesion pair using energy flow from the energy source, wherein the fourth lesion is formed in a fourth zone of the plurality of contiguous ablation zones, wherein the fourth lesion is the next sequential lesion formed after the third lesion, and wherein the fourth zone is not adjacent to the third zone;

count a second number of passed-over ablation zones between the lesions in the second lesion pair; and increment the cumulative sum of passed-over ablation zones by the second number to create an adjusted cumulative sum of passed-over ablation zones; and wherein the central controller is further configured, during the reporting out step, to report out the indication of the continuity of the isolation line based at least in part on the adjusted cumulative sum of passed-over ablation zones.

16. A control system for determining the continuity of an isolation line formed by point contact ablation in a region of the human heart, the control system configured to be operatively coupled with an energy source, the control system comprising:

a central controller configured to:

store a desired isolation line;

divide the desired isolation line into a plurality of contiguous ablation zones along the desired isolation line;

execute the following forming and counting steps:

forming a first lesion of a lesion pair using energy flow from the energy source, wherein the first lesion is formed in a first zone of the plurality of contiguous ablation zones;

forming a second lesion of the lesion pair using energy flow from the energy source, wherein the second lesion is formed in a second zone of the plurality of contiguous ablation zones, wherein the second lesion is the next sequential lesion formed after the first lesion, and wherein the second zone is not adjacent to the first zone;

counting a number of passed-over ablation zones between the lesions in the lesion pair; and incrementing a cumulative sum of passed-over ablation zones by the number; and report out an indication of the continuity of the isolation line based at least in part on the cumulative sum of passed-over ablation zones; and wherein the central controller is further configured, during the dividing step, to divide the desired isolation line into more than eight ablation zones.

* * * * *